(12) United States Patent
Irarrazabal Muñoz

(10) Patent No.: US 9,631,237 B2
(45) Date of Patent: Apr. 25, 2017

(54) METHOD FOR MONITORING, DIAGNOSIS AND/OR PROGNOSIS OF HYPOXIA RELATED DISORDERS USING NFAT5

(71) Applicant: UNIVERSIDAD DE LOS ANDES, Santiago (CL)

(72) Inventor: Carlos Ernesto Irarrazabal Muñoz, Santiago (CL)

(73) Assignee: UNIVERSIDAD DE LOS ANDES, Santiago (CL)

( * ) Notice: Subject to any disclaimer, the term of this patent is extended or adjusted under 35 U.S.C. 154(b) by 0 days.

(21) Appl. No.: 14/349,581

(22) PCT Filed: Oct. 3, 2012

(86) PCT No.: PCT/IB2012/055311
§ 371 (c)(1),
(2) Date: Apr. 3, 2014

(87) PCT Pub. No.: WO2013/050950
PCT Pub. Date: Apr. 11, 2013

(65) Prior Publication Data
US 2014/0255947 A1    Sep. 11, 2014

Related U.S. Application Data

(60) Provisional application No. 61/542,446, filed on Oct. 3, 2011.

(51) Int. Cl.
| | | |
|---|---|---|
| *G01N 31/00* | (2006.01) |
| *G01N 33/53* | (2006.01) |
| *C12Q 1/68* | (2006.01) |
| *G01N 33/68* | (2006.01) |

(52) U.S. Cl.
CPC ....... *C12Q 1/6883* (2013.01); *G01N 33/6872* (2013.01); *G01N 2800/28* (2013.01); *G01N 2800/324* (2013.01); *G01N 2800/7038* (2013.01)

(58) Field of Classification Search
CPC ............ C12Q 2600/158; C12N 15/113; C12N 2310/14; C07K 14/4702; A61K 31/56; A61K 31/58
See application file for complete search history.

(56) References Cited

U.S. PATENT DOCUMENTS

| | | | |
|---|---|---|---|
| 2008/0039416 A1* | 2/2008 | Ho | ..................... G01N 33/5011 |
| | | | 514/44 A |
| 2010/0178283 A1 | 7/2010 | Kalluri | |
| 2011/0183006 A1 | 7/2011 | Yamka et al. | |

FOREIGN PATENT DOCUMENTS

| | | |
|---|---|---|
| JP | 2010-187469 A | 8/2010 |
| WO | 2005026740 A1 | 3/2005 |
| WO | 2007114449 A1 | 10/2007 |
| WO | WO 2011/057172 A1 | 5/2011 |

OTHER PUBLICATIONS

International Search Report and Written Opinion issued in International Patent Application No. PCT/IB2012/055311, dated Apr. 16, 2013.
Extended European Search Report dated Feb. 11, 2016 issued by the European Patent Office for EPC Application No. 13817478.4.
NFAT5 is Activated by Hypoxi: Role in ischemia and reperfusion in the rat kindney, vol. 7, No .7, E39665, Jul. 2012, pp. 1-10—Villanueva S. et al.
Intrauterine growth restriction modifies the normal gene expression inkidney from rabbit fetuses Early Hum. Dev., vol. 88, No. 11, Sep. 1, 2012, pp. 899-904, Figueroa H. et al.
Increased NFAT5 expression stimulates transcription of Hsp70 in preeclamptic placentas, Placenta, vol. 35, No. 2, Dec. 21, 2013, pp. 109-116.

* cited by examiner

*Primary Examiner* — Lisa Cook
(74) *Attorney, Agent, or Firm* — Procopio, Cory, Hargreaves & Savitch LLP; Noel C. Gillespie

(57) ABSTRACT

The present invention relates to a method for monitoring, diagnosis and/or prognosis of hypoxia related disorders using NFAT5. The invention further comprises a diagnostic kit for determining the presence and/or level of NFAT5.

9 Claims, 15 Drawing Sheets

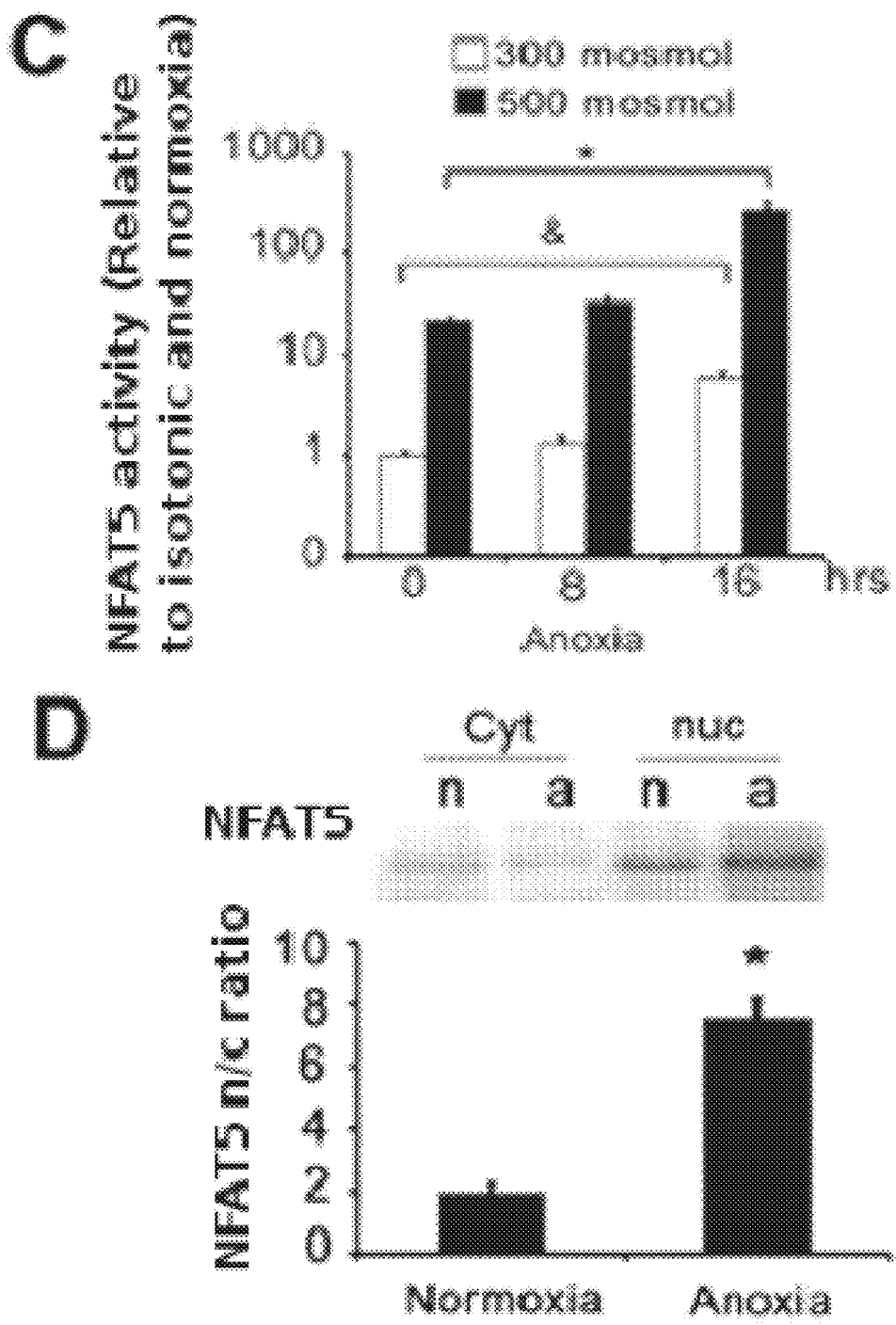
Figure 1C-D

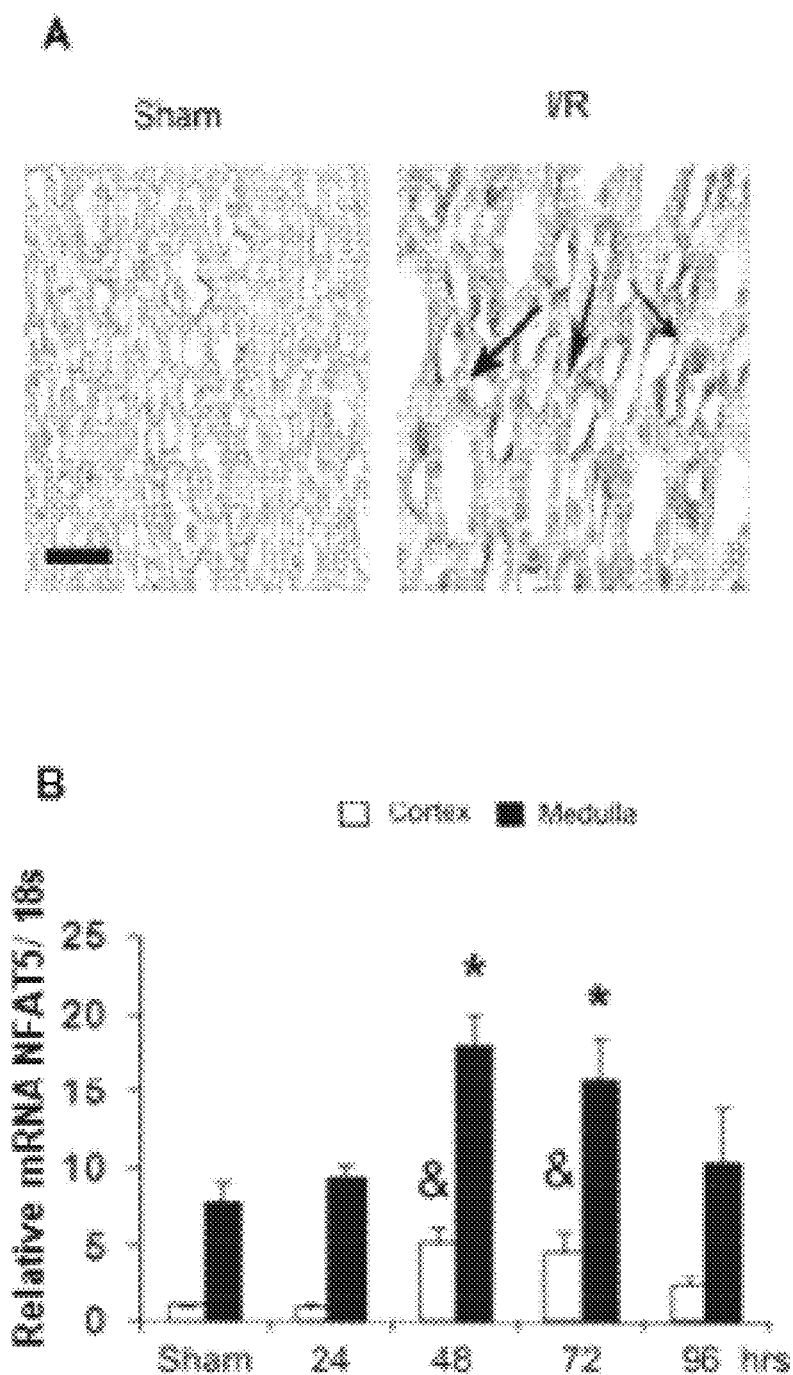
Figure 6 A-B

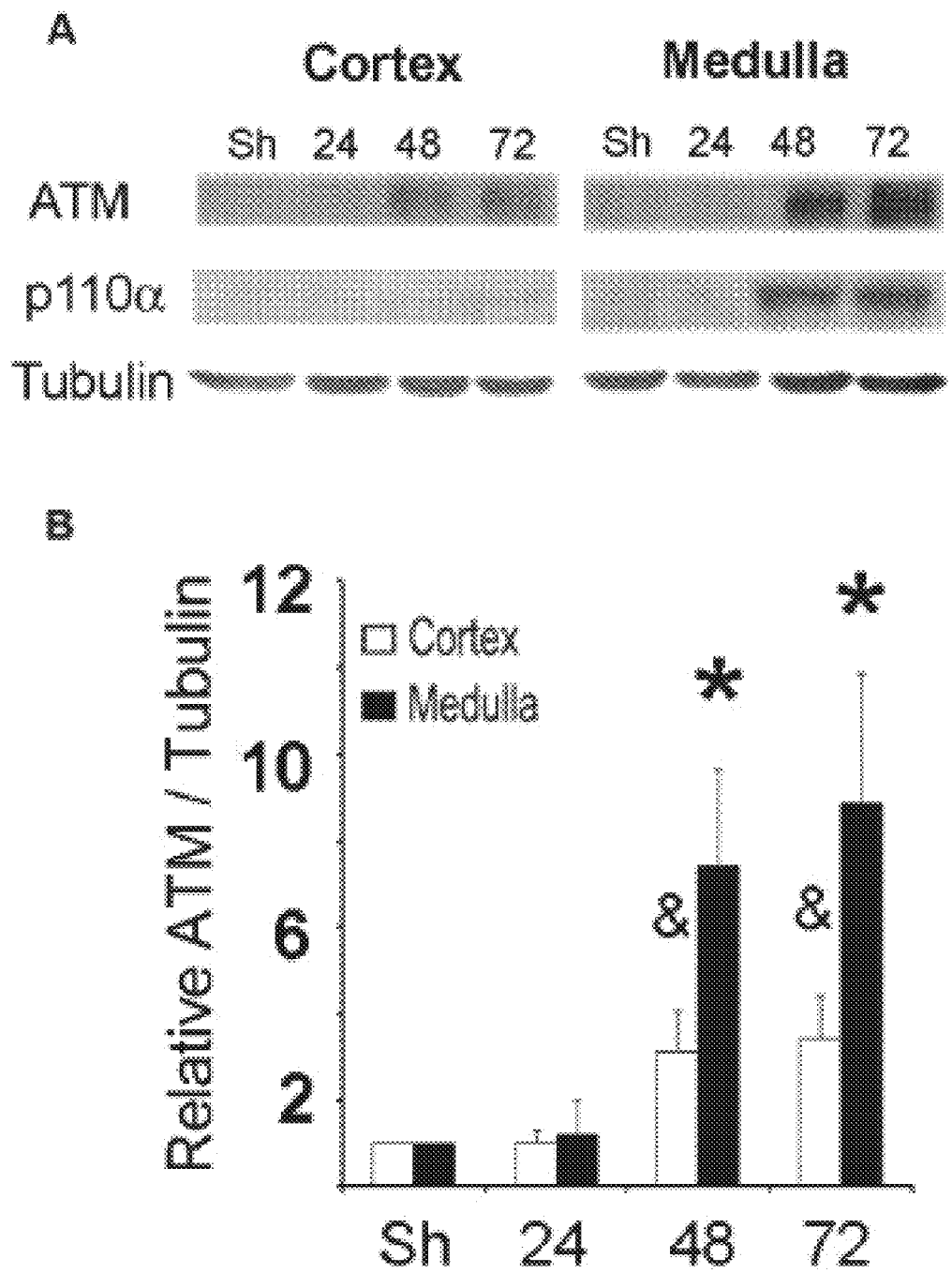
Figure 8 A-B

METHOD FOR MONITORING, DIAGNOSIS AND/OR PROGNOSIS OF HYPOXIA RELATED DISORDERS USING NFAT5

CROSS-REFERENCE TO RELATED APPLICATIONS

This patent application is the U.S. national phase of International Patent Application No. PCT/IB2012/055311, filed Oct. 3, 2012, which claims the benefit of U.S. Provisional Patent Application No. 61/542,446, filed on Oct. 3, 2011, and the contents of the foregoing applications are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,467 bytes ASCII (Text) file named "716531SequenceListing.txt," created Apr. 2, 2014.

FIELD OF THE INVENTION

The present invention relates to a method and a kit for monitoring, diagnosis and/or prognosis of hypoxia related disorders using NFAT5.

BACKGROUND OF THE INVENTION

Nuclear factor of activated T-cells 5 (NFAT5, TonEBP, or OREBP), is a human gene that encodes a transcription factor that regulates the expression of genes involved in the osmotic stress.

The NFAT5 protein is basically expressed in all tissues and cellular types, particularly in tissues that are often subjected to osmotic stresses, such as kidneys, eyes, and skin. The molecular mechanism of NFAT5 response in osmotic stress is well known, but NFAT5 is also involved in other biological roles, such as in embryonic development, in integrin-induced cell migration, in cellular proliferation. The mechanism by which NFAT5 acts in these other processes is currently not well known.

The NFAT5 (Nuclear factor of activated T-cells 5) has been identified as the transcription factor necessary for survival of renal cells in the challenging conditions of renal medulla (Miyakawa H, 1999; Woo S K, 2000b). The NFAT5 protein is highly expressed in renal medulla (Sykes, 2007). Knockout by disruption of both alleles in mice is typically embryonically lethal, and surviving NFAT5-null mice have profound and progressive atrophy of the renal medulla (Lopez-Rodriguez C, 2004). Transgenic (Tg) mice that overexpress OREBPdn (dominant negative form of TonEBP) specifically in the epithelial cells of the renal collecting tubules have impaired ability to concentrate urine, and show progressive atrophy of the renal medulla and cortical thinning, which in the most severe cases is accompanied by severe hydronephrosis and loss of medullary structure (Lam A, 2004).

NFAT5 is a member of the Rel family of transcriptional activators, which includes nuclear factor κB (NFκB) and the nuclear factor of activated T-cells (NFAT). Hypertonicity increases NFAT5 mRNA in MDCK (Woo S, 2000b), HeLa (Ko B C, 2000) and mouse inner medullary collecting duct (mIMCD3) cells (Cai Q, 2005). Hypertonicity transiently increases NFAT5 mRNA and protein abundance (Woo S, 2000a), peaking 4-12 h after hypertonicity depending on cell type. At 300 mOsm, NFAT5 is present in the nucleus and cytoplasm, but after hypertonicity it moves rapidly into the nucleus, inducing its transcriptional activity. In the rat kidney, nuclear localization of NFAT5 is decreased after water loading and increased after dehydration (Cha J H, 2001). The NFAT5 target gene contains at least one osmotic response element (ORE) consensus (Ferraris J, 1994; Ferraris J, 1996; Ferraris J, 1999; Woo S, 2000a; Dahl S C, 2001) and AP-1 site (Irarrazabal C, 2008). Additionally, high NaCl increases NFAT5 transactivating activity (Ferraris J, 2002a; Irarrazabal C E, 2010). NFAT5 activation by hypertonic stress results in the induction of several genes implicated in osmotic tolerance, such as aldose reductase (AR) (Burg M, 2007).

There are positive and negative (Colla E, 2006; Chen Y, 2007) upstream molecular regulators of the tonicity-dependent activation of NFAT5 transactivating activity. Positive regulators include: cAMP-dependent kinase (PKA) (Ferraris J, 2002b); p38 mitogen-activated protein kinase (MAPK) (Ko B C, 2002); Fyn, a member of the SRC family of non-receptor, cytoplasmic protein tyrosine kinases (Ko B C, 2002); Ataxia Telangiectasia Mutated (ATM) (Irarrazabal C, 2004, Zhang Z, 2005); phosphatidyl 3-kinase Class IA (PI3K-IA) (Irarrazabal C, 2006) and PLCγ1 (Irarrazabal 2010). Experiments using HEK293 and Jurkat cells demonstrate that the PI3-K class IA is upstream of ATM in high NaCl-induced activation of NFAT5 (Irarrazabal C, 2006).

The current paradigm postulates that NFAT5 presents tonicity-dependent activation dependent on oxidative stress: antioxidants that reduce ROS suppress high NaCl-induced activation of NFAT5 transcriptional activity (Zhou X, 2005; Zhou X, 2006). The urine concentrating mechanism in the kidney implies an increased osmolality, associated with low Pa02, allowing reactive oxygen species (ROS) to increase (Rosas-Rodríguez J A, 2010). On the other hand, there is evidence suggesting that ATM (NFAT5 regulator) is activated during hypoxia and hypoxia-reoxygenation in cancer cells (Hammond E M, 2004; Bencokova Z, 2009). However there is no information about the effect of hypoxia on NFAT5. We hypothesize that low oxygen concentration could induce NFAT5 activation. To study the effect of low oxygen on NFAT5 expression and activity we used primary cultures of rat IMCD and HEK293 cells, grown in isotonic and hypertonic media. We also analyzed the effect of hypoxia on cell death when NFAT5 was knocked down. Additionally, we tested the in vivo effect of hypoxia on NFAT5 activity in an experimental model of renal ischemia/reperfusion (I/R) in the rat. In the I/R kidneys we measured the mRNA and protein abundance of NFAT5, one of its downstream genes (aldose reductase, AR) and two of its upstream activators (ATM and PI3K). Our results show that NFAT5 is activated in vitro and in vivo by hypoxia and ischemia/reperfusion.

Myocardial infarction (MI) is the major cause of death and disability worldwide and continues to be a major public health problem despite considerable advances in diagnosis and management over the last decades (Thygesen K, 2007). The main determinants of patient outcome following MI are myocardial infarct size and left ventricular (LV) remodelling. Whereas infarct size is determined in the acute phase following MI, LV remodelling is a chronic maladaptive process, characterized by myocardial hypertrophy, fibrosis, progressive ventricular dilatation, and deterioration of cardiac performance over time, which eventually leads to congestive heart failure. One of the elements involved in the ischemic condition of MI is the hypoxia and there is not information about the role of NFAT5 during MI.

In general, the adult central nervous system (CNS) possesses a limited capacity for regeneration after injury, including ischemia. Following ischemic injury, neural tissue recovery is accompanied by the formation of reactive astrogliosis; this process is vital for isolating necrotic tissue from its uninjured surroundings, but concurrently, it markedly impedes regenerative processes. Shortly after ischemia, a series of ionic, neurotransmitter and oxidative radical imbalances occurs that lead to the activation of microglia and subsequently to an increased number of reactive astrocytes. Both cell types release cytokines and other soluble products (Tian D S, 2007) that play an important role in consecutive processes, including the apoptosis of oligodendrocytes (Yang Y, 2011) and neurons (Pettigrew L C, 2008). There is no information about the potential role of NFAT5 during hypoxia in CNS.

STATE OF THE ART

Document WO2007114449A1 published on 2007 discloses that the low-glucose and low-glucose-and-hypoxia environment surrounding a tumor also contributes to its resistance to chemotherapy, and inhibition of low-glucose-induced gene leads to the apoptosis of tumor cells. The document provides microarrays for detection of a low-glucose microenvironment or a low-glucose-and-hypoxia microenvironment, a method of treatment of solid tumors and a method of detections of solid tumors. The document mentioned that NFAT5 is activated in low-glucose-and-hypoxia conditions. We found that activation of NFAT5 is independent from glucose concentration, therefore, the method and kit of the present invention can identify a broader range of disorders that are associated to hypoxia dependent or independent from glucose level. The method and kit of the present invention is a faster, easier and cheaper way to detect hypoxia related disorders, since it involves only the determination of the presence and/or level of NFAT5 in a body fluid properly treated, and it does not require the use of a microarray involving a group of genes or proteins. The present invention also shows that NFAT5 can response to more extreme hypoxia conditions than HIF1, because in HEK293 cells (4 hours of hypoxia), NFAT5 induction was maximal at 1% $O_2$, nevertheless the induction of HIF1 was maximal at 2.5% $O_2$, despite it is induced at 1% $O_2$. On the other hand NFAT5 is induced by hypertonicity and hypoxia, but HIF1 is induced only by hypoxia, therefore, NFAT5 has a more general response to different noxae. Furthermore, NFAT5 is basically expressed in all tissues, and HIF1 is not. This situation allows NFAT5 to react faster than HIF1 to the noxa. Finally, we found that the NFAT5 activation by hypoxia is independently of HIF1.

The scientific works "Comparative evaluation of molecular-clinic markers of early renal injury in kidney transplant" and "Urinary exosomes, a new substrate for searching biomarkers of early renal dysfunction in kidney transplant" exposed in the XXVI Congress of Nephrology-Hypertension-Transplant (Chile, November 2009), disclose previous researches from the inventor of the present invention. NFAT5 was determined as an acute kidney injury biomarker, nevertheless in the present invention, NFAT5 has a broader application, as a biomarker for any disorder associated with hypoxia, such as, but not limited to, stroke, heart attack, cancer, cardiac disorders, occlusive circulative disorders, arteriosclerosis, myocardial infarction, ischemic-reperfusion-related-disorders, diabetic retinopathy, rheumatoid arthritis, conditions associated with organ transplant, inflammatory disorders, neonatal distress, isehemia, anemia, infections, and intrauterine growth retardation.

SUMMARY OF THE INVENTION

The present invention relates to a method for monitoring, diagnosis and/or prognosis of hypoxia related disorders using NFAT5, the method comprising the steps of a) providing a body sample; b) concentrating the transcription factors present in the sample; c) detecting and/or quantifying NFAT5 in the treated sample.

The invention further comprises a diagnostic kit for determining the presence and/or level of NFAT5, for simple determination of the onset of an hypoxia related disorder or condition in a subject, the kit comprising means for concentrating the transcription factors present in the sample and means for detecting NFAT5.

DETAILED DESCRIPTION OF THE INVENTION

The present invention relates to a method for monitoring, diagnosis and/or prognosis of hypoxia related disorders using NFAT5, the method comprising the steps of a) providing a body sample; b) concentrating the transcription factors present in the sample; c) detecting and/or quantifying NFAT5 in the treated sample.

In one embodiment, the body sample is blood, urine, gingival crevicular fluid, saliva, sinovial fluid, and/or amniotic fluid.

The present invention considers as means for concentrating the transcription factors present in the sample, laboratory methods and devices useful in separating, larger elements from the sample, which could interfere in the detection phase later. For example, the interfering elements can be cells from the patient. Immunopurification and/or immunoprecipitation methods can be consider as concentrating means. Centrifugation and ultracentrifugation can be considered as concentrating means. Centrifuge tubes can be considered concentrating means, since the processing in a laboratory centrifuge allows to eliminate larger particles, such as for example cells. In one embodiment, the sample is centrifuged for 5 to 30 minutes at 5000 to 10000 rpm. In another embodiment, the sample is ultracentrifuged for 30 to 120 minutes at 30000 to 45000 rpm.

Microfiltration can be considered as concentrating means. Microfilter cartridges, microfilter columns, or other microfilter media, up to 0.22 µm are also considered as concentrating means.

In another embodiment of the invention, the method considers, as means for detecting and/or quantifying NFAT5, a primary antibody directed to NFAT5, and a secondary antibody conjugated with a label, directed to the primary antibody. The label of the secondary antibody can be a fluorescent marker, an enzyme, a radioactive marker, a chemical compound, and/or an infrared compound.

Optionally, the primary antibody can be conjugated directly with a label, in which case, the secondary antibody is not needed. The primary antibody can be also conjugated with a fluorescent marker, an enzyme, a radioactive marker, a chemical compound, and/or an infrared compound.

The method optionally includes a step for evaluating an hypoxia related condition and/or disorder in a subject for monitoring, diagnosis, prognosis and/or determining a treatment in the subject based on the presence and/or level of NFAT5.

NFAT5 can be used as a biomarker for any disorder associated with hypoxia, such as, but not limited to, stroke, heart attack, cancer, cardiac disorders, occlusive circulative disorders, arteriosclerosis, myocardial infarction, ischemic-reperfusion-related-disorders, diabetic retinopathy, rheumatoid arthritis, conditions associated with organ transplant, inflammatory disorders, neonatal distress, ischemia, anemia, infections, and/or intrauterine growth retardation.

Table 1 presents some conditions associated with hypoxia that can be evaluated using NFAT5 determination and the body fluid where NFAT5 must be determined.

TABLE 1

Conditions associated with hypoxia and body fluid associated.

| Condition | Body fluid |
| --- | --- |
| Stroke | blood/urine |
| Heart attack | blood/urine |
| Cancer | blood/urine |
| Cardiac disorders | blood/urine |
| Occlusive circulative disorders | blood/urine |
| Arteriosclerosis | blood/sinovial fluid |
| Myocardial infarction | blood/urine |
| Ischemic-reperfusion-related-disorders | blood/urine |
| Diabetic retinopathy | blood/urine |
| Rheumatoid arthritis | blood/sinovial fluid |
| Conditions associated with organ transplant | blood/sinovial fluid |
| Inflammatory disorders | blood/urine |
| Neonatal distress | blood/urine/amniotic fluid |
| Ischemia | blood/urine |
| Anemia | blood/urine |
| Infections | blood/urine/saliva/gingival crevicular fluid |
| Intrauterine Growth Retardation | blood/urine/amniotic fluid |

The invention further comprises a diagnostic kit for determining the presence and/or level of NFAT5, for simple determination of the onset of an hypoxia related disorder or condition in a subject, the kit comprising means for concentrating the transcription factors present in a body sample and means for detecting and/or quantifying NFAT5.

In one embodiment, the body sample is blood, urine, gingival crevicular fluid, saliva, sinovial fluid, and/or amniotic fluid.

Optionally, the diagnostic kit comprises means for obtaining a body sample from a patient. In a particular embodiment, the means for obtaining the body sample are selected, but not limited to, a urinary probe, a container to receive a urine sample, needles, preferably vacutainer needles, tubes, and syringes or a combination thereof.

The kit of the present invention includes means for concentrating the transcription factors present in the sample. Immunopurification and/or immunoprecipitation means are considered concentrating means, thus in one embodiment, the kit of the present invention comprises antibodies, and suitable reaction buffer to allow the antibodies to interact with the domains of proteins they are directed to. The kit also comprises blocking agents or solutions and stock solutions of NFAT5. In another embodiment, the kit can also comprises centrifuge tubes, microfilter cartridges, microfilter columns, other microfilter media, up to 0.22 micrometers, or combination thereof, to be used in laboratory methods and devices useful in separating larger elements from the sample, that can be considered concentrating means.

In another embodiment of the invention, the kit considers, as means for detecting and/or quantifying NFAT5, a primary antibody directed to NFAT5, and a secondary antibody conjugated with a label, directed to the primary antibody. The label of the secondary antibody can be a fluorescent marker, an enzyme, a radioactive marker, a chemical compound, and/or an infrared compound.

Optionally, the primary antibody can be conjugated directly with a label, in which case, the secondary antibody is not needed. The primary antibody can be also conjugated with a fluorescent marker, an enzyme, a radioactive marker, a chemical compound, and/or an infrared compound.

The kit of the invention optionally comprises instructions for using the kit.

EXPERIMENTAL SECTION

Figure 1A:
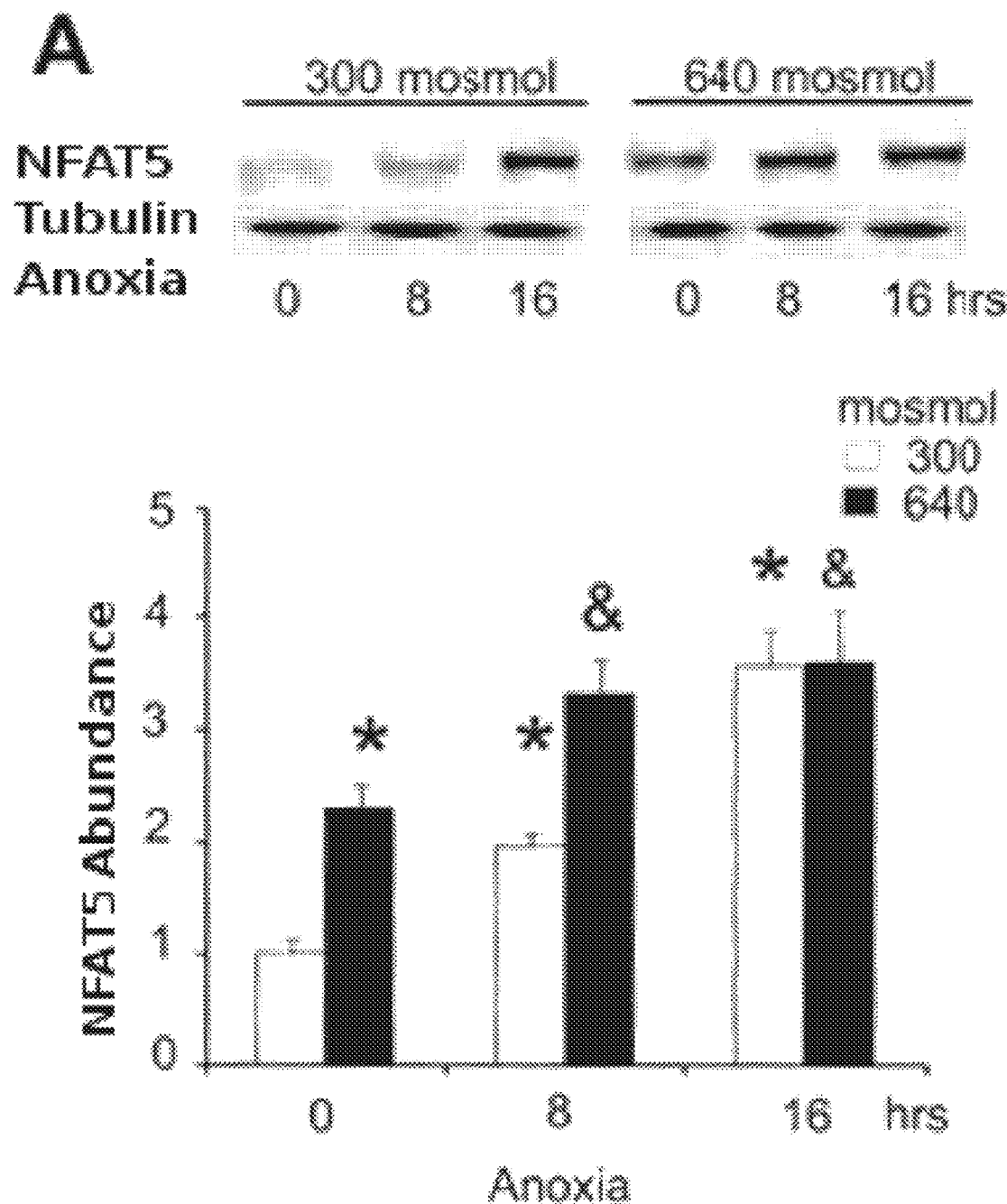
FIG. 1: Anoxia increases NFAT5 protein abundance and promotes nuclear translocation. A. Rat primary IMCD cells in isotonic (300 mOsM) or hypertonic (640 mOsM) medium were exposed to anoxia (replacement of $O_2$ by $N_2$) for 0, 8, or 16 hrs. We prepared total protein homogenates and determined NFAT5 protein abundance by Western blot. A representative picture is shown in the upper section and the graph shows mean±SEM. * or & P≤0.05; n=5. (*vs 300 mosmol/normoxia and & vs 640 mosmol/normoxia). B. NFAT5 cellular distribution after 2 hrs of anoxia evaluated in primary IMCD cells by immunofluorescence. B1: NFAT5 labelling (Alexa488); B2: nuclei (Hoechst); B3: Merge. C. HEK293 cells stably expressing ORE-X (a specific reporter gen of NFAT5) cultured at 300 mosmol or 500 mosmol by 16 hrs; during this time the cells were exposed for 0, 8 or 16 hrs to anoxia, and luciferase reporter assay was used to evaluate transcription activity; Mean±SEM. (* or &, P<0.05; n=5). D. HEK293 cells cultured at 300 mosmol were exposed by 2 hrs to anoxia (a) or normoxia (n). Nuclear and cytoplasmatic fractions were separated by NE-PER and NFAT5 abundance was determined by Western blot. Bar graph represents Mean±SEM. * indicates P<0.05; n=5.

In this section illustrative examples are given as guidance, therefore, these examples are in no way to be construed as limiting Example 1

NAFT5 is Induced in Renal Hypoxia

Animals.

Adult male Sprague-Dawley rats (250 g, n=5 for each I/R group: 24 hrs, 48 hrs, 72 hrs and 96 hrs) were housed in a 12 hrs light/dark cycle. Animals were weighed at the time of initiation of bilateral ischemic injury and after completion of experiments. The animals had food ad libitum and controlled water and were maintained at the University animal care facility. All experimental procedures were in accordance with institutional and international standards for the humane care and use of laboratory animals (Animal Welfare Assurance Publication A5427-01, Office for Protection from Research Risks, Division of Animal Welfare, The National Institutes of Health).

Renal Ischemia/Reperfusion Injury.

Animals were anesthetized with ketamine:xylazine (25:2.5 mg/kg, ip), maintaining a body temperature of 37° C. Both kidneys were exposed by a flank incision, and both renal arteries were occluded with a non-traumatic vascular clamp for 30 minutes. After 30 minutes of clamping, clamps were removed, renal blood flow was re-established, both incisions were sutured, and rats were allowed to recover in a warm room. Rats were euthanized under anesthesia (ketamine:xylazine) 24, 48, 72 and 96 hrs after reperfusion; both kidneys were removed and processed for immunohistochemistry, real time PCR and Western blotting (Irarrazahal C, 2006; Villanueva V, 2006). A group of sham animals were included; the kidneys of these animals were exposed by a flank incision, but they did not receive renal artery occlusion.

Cell Culture and Treatment

Primary cultured cells were obtained from the inner renal medulla of male Sprague-Dawley rats (120-150 g body weight). The papillary tissue was finely minced with a surgical blade under sterile conditions. The tissue was digested into a 10 ml culture medium (DMEM/Ham's F12, 5 mg/ml transferring, 5 mg/ml human insulin, 50 nM hydrocortisone, 5 µM triiodothyronin, 50 UI/ml penicillin and 50 mg/ml streptomycin) plus 20 mg collagenase and 7 mg hialuronidase at 37° C. in a shaker for 90 minutes. After the tube was centrifuged at 1000 rpm for 1 minute, the supernatant was discarded and the pellet was suspended in DMEM/Ham's P12. This procedure was repeated 3 times. Finally, the pellet was suspended in culture medium with 10% fetal bovine serum (EBS) and cultured in a 30 mm culture dish. Cells were incubated at 37° C. in a 5% CO? atmosphere. HEK293 cells and HEK293 cells stably expressing ORE-X (a specific reporter gen of NPAT5, HEK293OREX; Irarrazabal C, 2006) were cultured in a 300 mosmol/kg medium according to ATCC (American Type Culture Collection, Manassas, Va.) instructions.

Hypoxia in Cell Cultures

Cultured cells were incubated in isotonic (300 mOsM) or hypertonic (500 or 640 mOsM) media for 24 hrs. NaCl was added to the isotonic culture media to make the solutions hypertonic. After 24 hrs of culture in isotonic or hypertonic media, cells were incubated in anoxic or hypoxic (2.5%) conditions for time course experiments (0, 4, 8 or 16 hrs at 37° C.). Hypoxic or anoxic conditions were obtained by replacing oxygen with $N_2$, using a Heracell 150i $CO_2$ incubator (Thermo Scientific).

Luciferase Assays

HEK293 cell were cultured as described above. The culture solution was harvested and the supernatant was recovered by centrifugation at 2000 rpm. HEK293-OREX cells (Irarrazabal C, 2004, 2006, 2010) were cultured in isotonic (300 mOsM) or hypertonic media (640 mOsM) for 16 hrs. In both osmotic conditions, the cells were exposed to anoxia (0, 8 or 16 hrs at 37° C.) as described above. Luciferase activity was measured with the Luciferase Assay System (Promega, Madison, Wis.) using the BiotexLuminometer. Luciferase activity was expressed in relative light units (RLU) per µg of total cell protein.

Lactic Dehydrogenase (LDH) Activity

LDH leakage into the culture medium was measured using LDH assay, based on NADH oxidation in the presence of LDH due to the transformation of pyruvate into lactate. NADH concentration was measured at 340 nm using the GeneQuantr™ 1300 Spectrophotometer (GE Healthcare).

Western Blot Analysis

Total protein was measured using the BCA Protein Assay Kit, (Pierce, Rockford, Ill.). Cortex and medulla kidney sections from one half kidney were homogenized with an Ultra-Turrax homogenizer in lysis buffer containing 50 mM Tris-HCl, pH 8.0, 150 mM NaCl, 1% Triton X-100, protease inhibitor (Complete Mini, Roche Applied Science, Indianapolis, Ind.), and phosphatase inhibitor cocktails (Phosphatase Inhibitor Cocktails 1 & 2, Sigma, St. Louis, Mo.). Tissue homogenates were then centrifuged (15,000×g, 10 min) and the supernatant was stored (−70° C.) for SDS_PAGE and Western blot analysis. Proteins were separated on 7.5 or 10% Tris-Glycine gels and transferred to nitrocellulose membranes (Invitrogen, Carlsbad, Calif.). Western blot analysis was performed according to standard conditions (Irarrazabal C, 2010). In brief, after blocking nonspecific binding, membranes were incubated with rabbit anti-NFAT5 (NFAT5) (Affinity BioReagents, Golden, Colo.), goat anti-AR (Santa Cruz Biotechnology, Santa Cruz, Calif.), rabbit anti-tubulin (Cell Signalling), anti-cleaved Caspase-3 (Asp 175) (Cell Signalling), anti-M30 CytoDEATH (ROCHE), anti-ATM (cell signalling), anti-phospho ATM (cell signalling), anti-p110alpha (Cell signalling), anti-AKT (Cell signalling), anti-phosphoAKT-308 (Cell signalling) or mouse anti-HIF1α (Abcam) antibody overnight at 4° C. After washing with 0.1% Tween-20 in PBS, blots were incubated with the appropriate horseradish peroxidase (HRP)-conjugated secondary antibody for 1 hour at room temperature. Proteins were detected using an enhanced chemiluminescence technique (PerkinElmer, Life Sciences, Boston, Mass.). The blots were scanned and densitometric analysis was performed using the public domain NIH Image program v1.61 (US National Institutes of Health, rsb.info.nih.gov/nihimage).

Fluorescence Microscopy.

First passage rat IMCD cells were grown in 8 well Chamber-Slides (Lab-Tek, Nunc). After 24 hours of culture in isotonic (300 mOsM) media, the tissue culture slides were incubated for 2 hrs in anoxia ($O_2$ replaced by $N_2$, Heracell 1.50i $CO_2$ incubator; Thermo Scientific). After this time the culture medium was quickly removed, the fixing reagent was added (100% of cold methanol) and cells were stored overnight at −20° C. Then, the cells were washed, incubated in the presence of blocking solution (1 hour, room temperature) and incubated with anti-NFAT5 antibody (1 hour, room temperature). After washing, the secondary antibody was added (1 hour Alexa 488-Green, 1:200 dilution, Invitrogen). Nuclei were stained with Hoechst (Sigma). The slides were mounted and NFAT5 cellular distribution was analyzed by fluorescence microscopy using an Olympus BX61WI upright microscope with an Olympus DSU spinning disk unit. Images were recorded with the cooled charge coupled device video camera (SIS-FVT2, OLYMPUS) and analyzed using the imaging software (CellM&CellR, OLYMPUS).

Immunohistochemical Analysis and Tissue Damage Determination.

Immunohistochemical studies in paraplast-embedded sections were carried out by tissue processing according to previously described methods. Briefly, tissue sections were dewaxed, rehydrated, rinsed in 0.05 M tris-phosphate-saline (TPS) buffer (pH 7.6) and incubated with the primary antibody overnight at 22° C. Afterwards, sections were washed three times for 5 minutes each, followed by 30 minute incubation at 22° C. with the corresponding secondary antibody and with the peroxidase-antiperoxidase (PAP) complex. Immunoreactive signals were revealed using 3,3'-diaminobenzidine 0.1% (wt/vol) and 0.03% (vol/vol) hydrogen peroxide solution. Periodic acid-Schiff (PAS) staining was used to determine tissue damage.

Real Time PCR

Total RNA was isolated using TRIzol (GIBCO, Life Sciences) as per manufacturer instructions. RNA concentration was determined by spectrophotometry and integrity of the RNA was assessed by agarose gel electrophoresis. cDNA was prepared from total RNA (0.5 µg) using a reverse transcription system (random hexamers, Improm II Reverse Transcriptase System; Promega). PCR was performed on 8 ng and 80 ng cDNA samples per 20:1 reaction in triplicate for each experiment (GoTaq Flexi DNA polymerase, Promega). Amplicons were detected for Real-Time Fluorescence Detection (Rotor-Gene Q, Qiagen). Primers used to qPCR were:

```
to aldose reductase (AR):
SEQ ID NO: 1:      5'ATTCGTCCACCACAGCTTCAGACT-3'
and
SEQ ID NO: 2:      5'AGCAATGAGGACATGGCCACTCTA-3;

to NFAT5:
SEQ ID NO: 3:      5'TTCATCTCATTGCTCAGCG-3'
and
SEQ ID NO: 4:      5'-GGGAGAAGATCATAGACAGATTC-3';

to HIF-1α:
SEQ ID NO: 5:      5'-ACCTCTGGACTTGCCTTTC-3'
and
SEQ ID NO: 6:      5'-TTTTTCTTGTCGTTCGCGC-3'.
and to 18S (housekeeping):
SEQ ID NO: 7:      5'-TTAGAGTGTTCAAAGCAGGCCCGA-3'
and
SEQ ID NO: 8:      5'TCTTGGCAAATGCTTTCGCTCTGG-3'.
```

The detection system records the number of PCR cycles (Ct) required to produce an amount of product equal to a threshold value, which is a constant. From the Ct values, we calculated the relative mRNA abundance in each experimental condition, and values were normalized to the relative abundance of each transcript in tissue from paired sham animals, as described (Irarrazabal C, 2010).

Statistical Analysis

Data are expressed as average±SEM. Values from different groups were assessed with the parametric Student's t-test when comparing two groups and Anova for multiple comparisons with a post-hoc Fisher's test when comparing more than two groups. The significance level was $p<0.05$.

Effect of Hypoxia on NFAT5.

Figure 8:
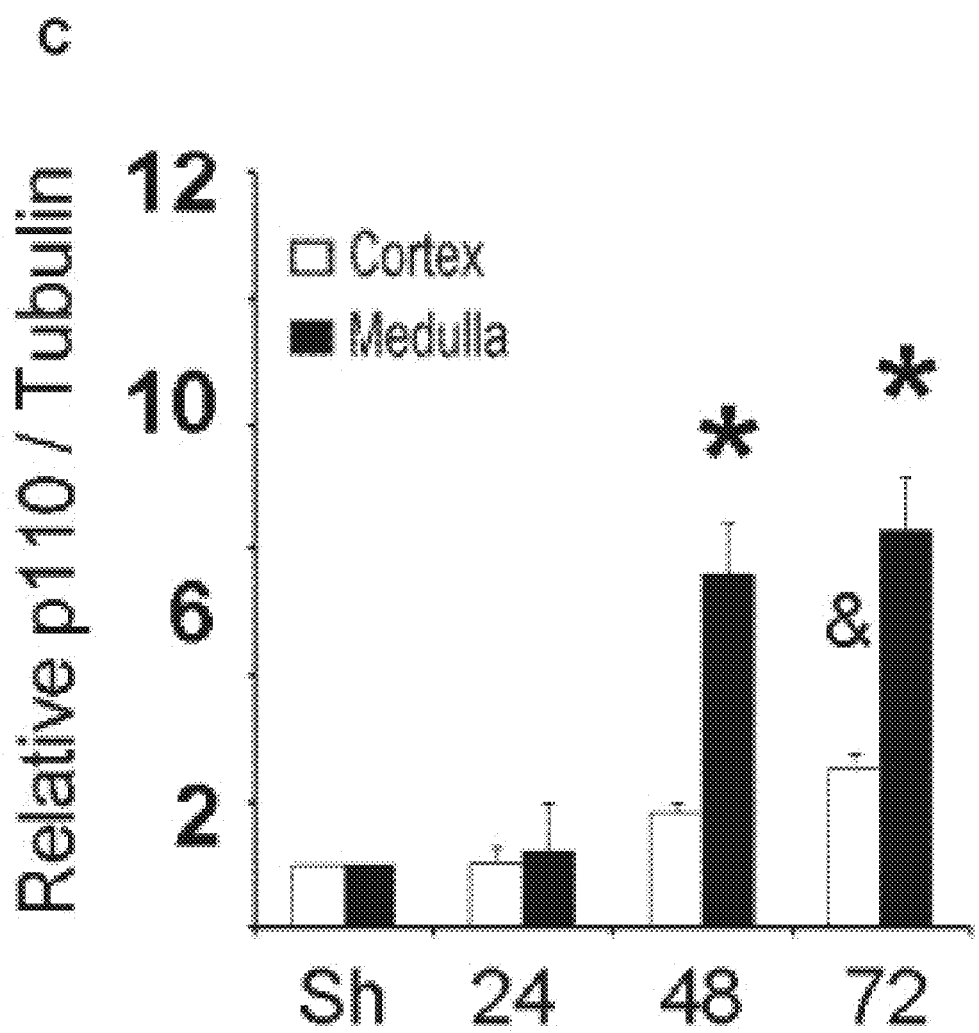
FIG. 8: NFAT5-regulators protein, ATM and PI3-K, were induced in post ischemic kidneys. ATM and PI3-K (p110α) protein abundance was measured by Western blot in cortex or medulla from rat kidney. A. A representative picture is shown in the upper section (n=5). B. Relative ATM abundance. C. Relative p110α abundance Mean±SEM. * or & indicates P<0.05; n=5 (* vs sham medulla & vs sham cortex).

We analysed the effect of anoxia on the NFAT5 protein abundance in primary cultures of inner medullary collecting duct (IMCD) cells from rat kidney. IMCD cells were cultured in isotonic (300 mOsM) or hypertonic (640 mOsM) media for 24 hrs. As expected, hypertonicity increased the NFAT5 abundance in primary IMCD cells (FIG. 1A, 0 hrs anoxia). In isotonic media, anoxia induced a NFAT5 protein abundance of 120 and 250% over the control, after 8 and 16 hrs of anoxia, respectively (FIG. 1A). In the hypertonic condition (24 hrs), 8 hrs of anoxia caused an additional induction of NFAT5 protein abundance (FIG. 1A, 8 hrs anoxia). Interestingly, 16 hrs of anoxia induced NFAT5 protein abundance independent of tonicity (FIG. 1A, 16 hrs anoxia).

Figure 1B:
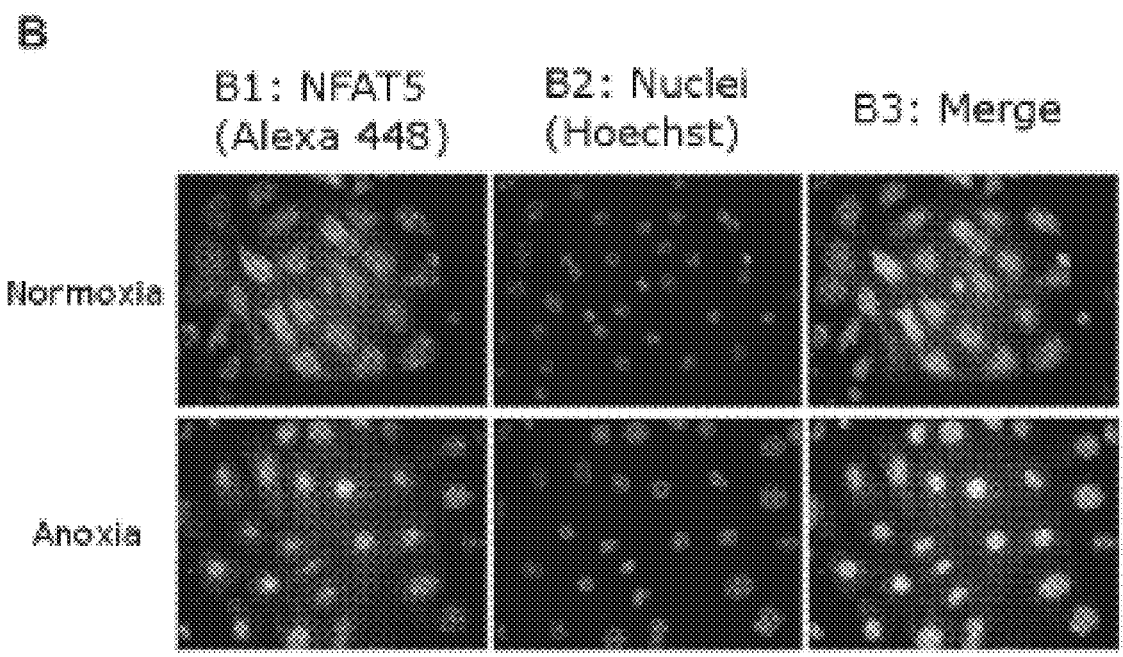

We tested the effect of low $PaO_2$ on NFAT5 activation. First we evaluated its nuclear translocation in primary IMCD cells under anoxia. Using fluorescence microscopy, we observed the NFAT5 nuclear localization induced after 2 hrs of anoxia (FIG. 1B), suggesting the NFAT5 activation at this time. Next, we evaluated the transcriptional activity of NFAT5 using HEK293OREX cells (stably expressing a reporter gene) (Irarrazabal C, 2010). In isotonic medium, 16 hrs of anoxia increased 4.6-fold the transcriptional activity of NFAT5 (FIG. 1C). In hypertonic medium, anoxia (16 hrs) induced 9.6-fold the transcriptional activity over the normoxia condition (21% oxygen and 500 mosmol; FIG. 1C). These results show that anoxia induced the NFAT5 transcriptional activity independent of tonicity. Using HEK293 cells and Western blot analysis, we confirmed the NFAT5 nuclear translocation caused by anoxia (FIG. 1D), observed with IMCD cells exposed to anoxia (FIG. 1B).

Figure 2:
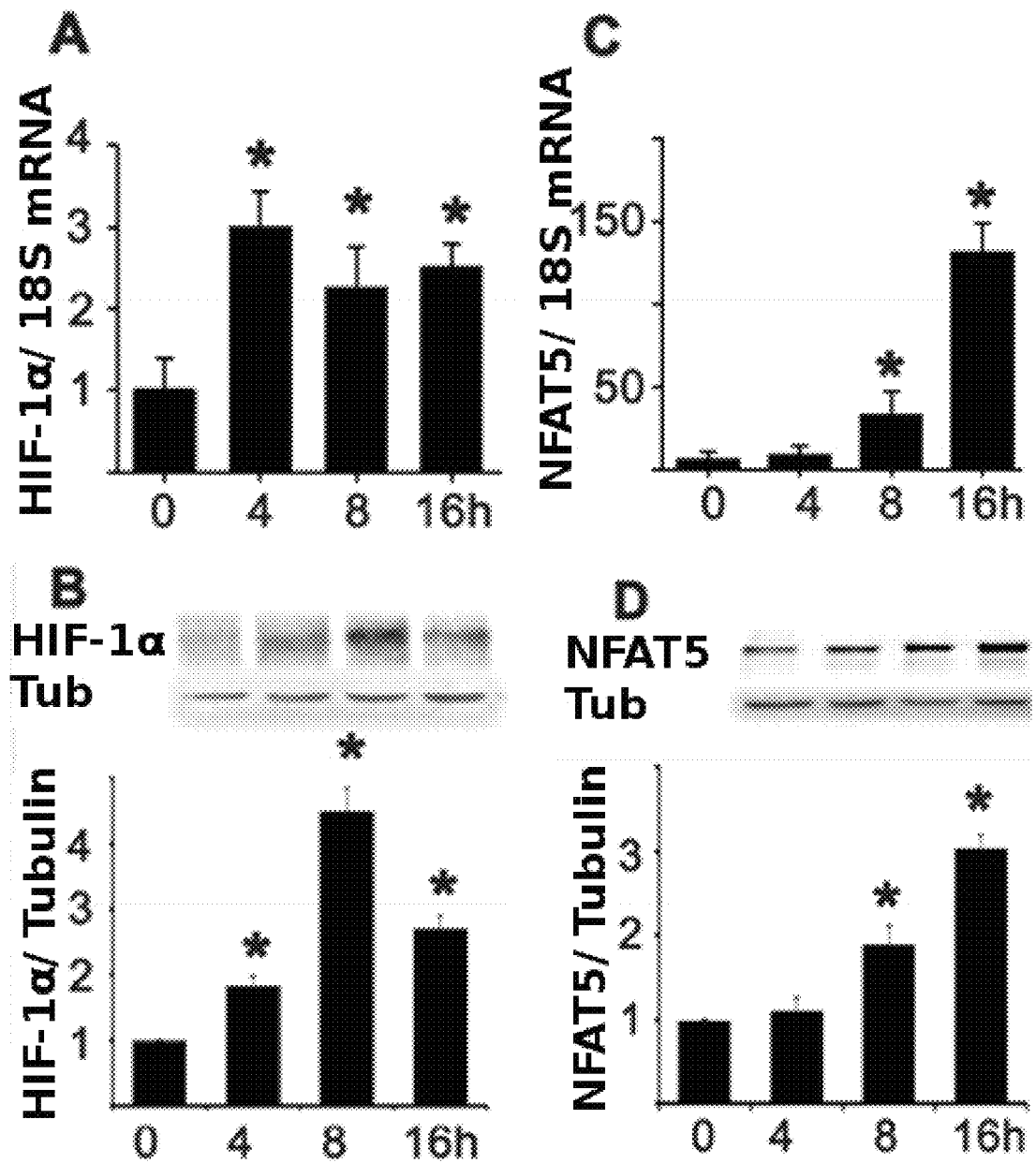
FIG. 2: Hypoxia induces NFAT5 later than HIF-1α. HEK293 cells cultured at 300 mosmol were exposed for 0, 4, 8, and 16 hrs to hypoxia (2.5% of PO2). HIF-1α gene expression was determined by qRT-PCR (A) and Western blot (B). NFAT5 gene expression was determined by qRT-PCR(C) and Western blot (D). Protein abundance was normalized by tubulin (Tub). Mean±SEM. *, P<0.05; n=5.

To gain some insight into the potential mechanisms leading to NFAT5 activation by low oxygen, we evaluated the time course of NFAT5 activation and the classical transcription factor induced by hypoxia (HIF-1α) in response to hypoxia (2.5% $O_2$). We observed induction of a mRNA and protein starting after 4 hrs of hypoxia, with a maximum at 8 hrs (2.5% $O_2$, FIGS. 2A and 2B). However, the induction of NFAT5 mRNA and protein was observed only after 8 hrs of hypoxia and continued increasing up to 16 hrs (FIGS. 2C and 2D). Next, we studied potential signalling pathways involved in NFAT5 activation by hypoxia. In previous studies, we have demonstrated that ATM and PI3-K (p110α) are two positive regulators of NFAT5 in response to high NaCl (Irarrazabal 2004, 2006). HEK293 cells exposed to hypoxia showed time-dependent activation of ATM, as indicated by increased ATM phosphorylation after 8 and 16 hrs of exposure to 2.5% $O_2$ (FIG. 3A). In addition to ATM, the PI3-K was also activated by hypoxia in HEK293 cells. We observed a significant increase in both p110α abundance and AKT-308 phosphorylation starting at 8 hrs of hypoxia (FIGS. 3B and 3C).

Figure 4:
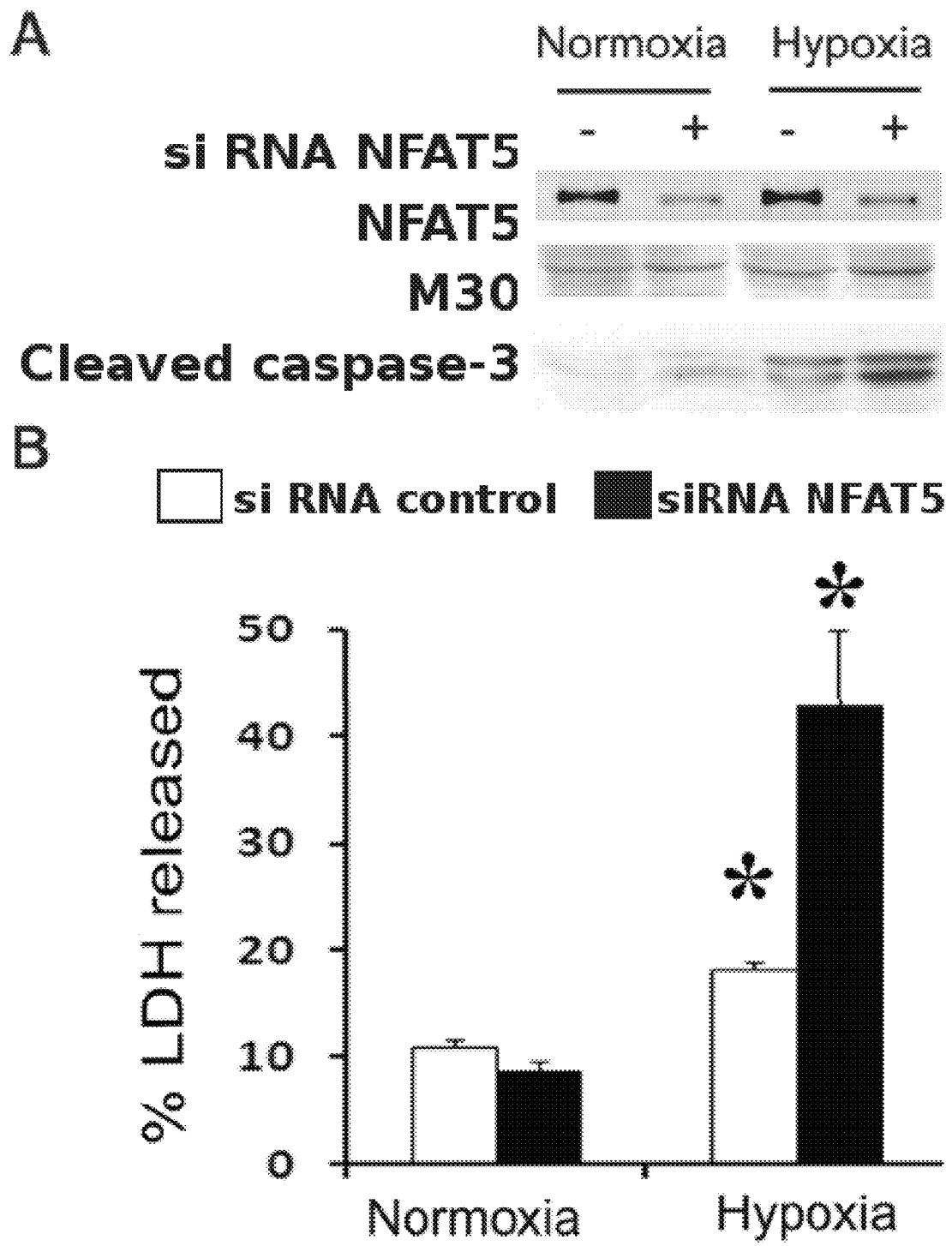
FIG. 4: NFAT5 has a protective role against hypoxia. HEK293 cells cultured at 300 mosmol were transfected with control and NFAT5 siRNA. 48 hrs after transfection the cells were exposed for 8 hrs to 2.5% $PO_2$. A. Western blot of NFAT5, M30 and cleaved caspase-3 were measured in cell lysate. B. Lactic dehydrogenase (LDH) activity was assayed in cell culture media by spectrometric determination of NAME Mean±SEM. *, P<0.05; n=5.

Since NFAT5 is a pro-survival factor in osmotic stress, we investigated the potential role of NFAT5 in cell tolerance to hypoxia. The transient transfection of HEK293 cells with NFAT5 siRNA decreased the protein abundance of this transcription factor, as compared with cell's transfected with scrambled siRNA (control, FIG. 4A). To estimate the apoptosis state in hypoxia, we measured cleaved caspase-3 and M-30 in HEK293 cells. Active caspases 3 and 9 target the K8/18 proteins of the cellular intermediate filaments network, and the M30 CytoDeath monoclonal antibody recognizes a neo-epitope exposed after the cleavage of K18 by caspases. In the apoptotic cascade, these events precede the loss of membrane asymmetry and DNA fragmentation. Cleaved caspase-3 and M-30 were increased after 8 hours of hypoxia in control-transfected cells; when NFAT5 was knocked down and cells were exposed to hypoxia, these two apoptotic markers were induced (FIG. 4A). We also evaluated cell death by measuring lactate dehydrogenase (LDH) activity in the culture media. LDH activity was increased in hypoxic cells (2.5% $O_2$, FIG. 4B). The knockdown of NFAT5 by siRNA increased LDH activity (FIG. 4B). These results suggest that NFAT5 has a protective role against cell death induced by hypoxia.

NFAT5 Expression in Kidney Exposed to Experimental FR.

We used morphological and functional analysis to evaluate the kidney injury in the experimental I/R in rat. Kidney sections stained with PAS showed alterations in kidney morphology from 48 hours after I/R (FIG. 5A). The most evident alterations were brush border flattening of the epithelia and a high percentage of cells undergoing mitosis in proximal tubule cells. These alterations were almost undetectable 96 hrs after I/R (data not shown). The I/R animals had higher serum creatinine levels than sham animals after 24 hrs of I/R (1.2 mg/dl; FIG. 5B), which recovered after 96 hrs. Urine concentration, as estimated by determination of the U/P osmolarity ratio, showed that experimental I/R animals excreted less concentrated urine than sham animals from 24 to 96 hrs of FR (FIG. 5C).

The hypoxia response activation was demonstrated previously, using the same model of experimental I/R in rat kidney (2-pimonidazole and HIF-1α; Villanueva S, 2006). NFAT5 expression was evaluated in kidneys from sham and experimental I/R animals by immunohistochemistry, qRT-PCR and Western blot. Immunohistochemical analysis of NFAT5 showed higher immunoreactivity in the renal medulla of I/R animals as compared with sham (FIG. 6A). The signal was increased in the nuclei of tubular and blood vessel cells (FIG. 6A; see arrows), suggesting NFAT5 activation in the kidney induced by ischemia and reperfusion.

Figure 6:
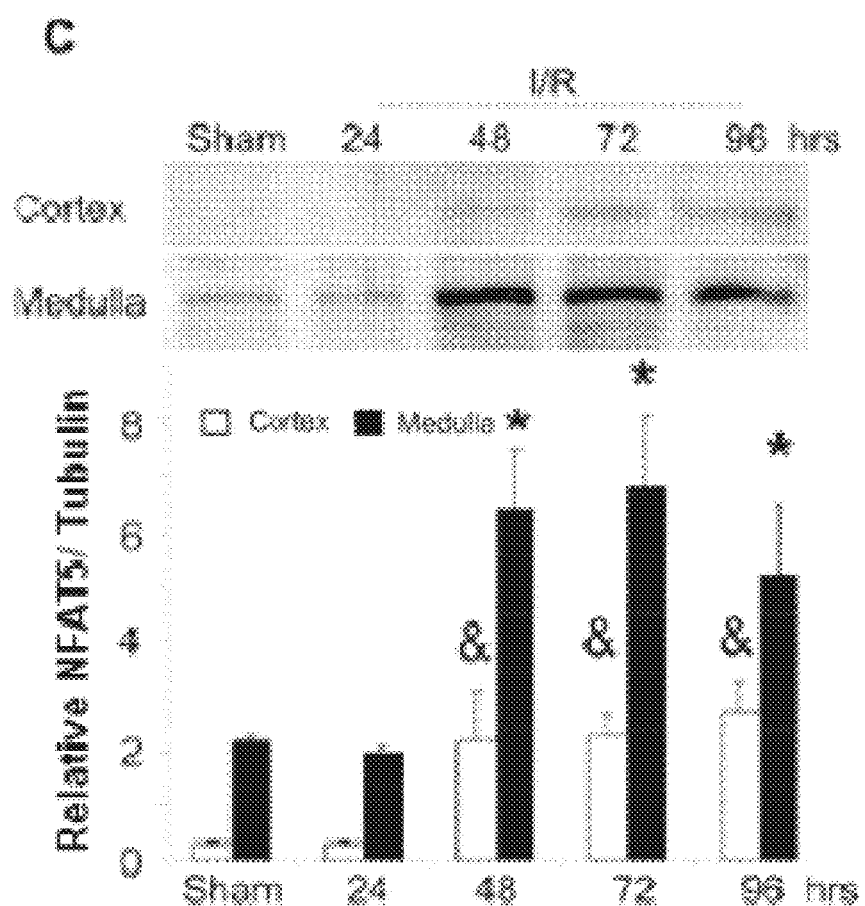
FIG. 6: NFAT5 and a are induced in post ischemic kidneys. A. Kidney sections of sham and I/R animals (72 hrs) were incubated with rabbit anti-NFAT5. Representative pictures of medulla from sham and I/R animals are shown. Preimmune serum did not stain significantly (data not shown). Scale bar=100 µm. The arrows indicate the localization of the corresponding marker for NFAT5. B. NFAT5 mRNA abundance in cortex and medulla of kidneys were determined by qRT-PCR. C. NFAT5 protein abundance in cortex and medulla of kidneys were determined by Western blot D. HIF-1α protein abundance in cortex and medulla of kidneys were determined by Western blot. A representative picture is shown in the upper section. All values are Mean±SEM. * or & indicates P<0.05; n=5 (* vs sham medulla and & vs sham cortex).
Figure 6:
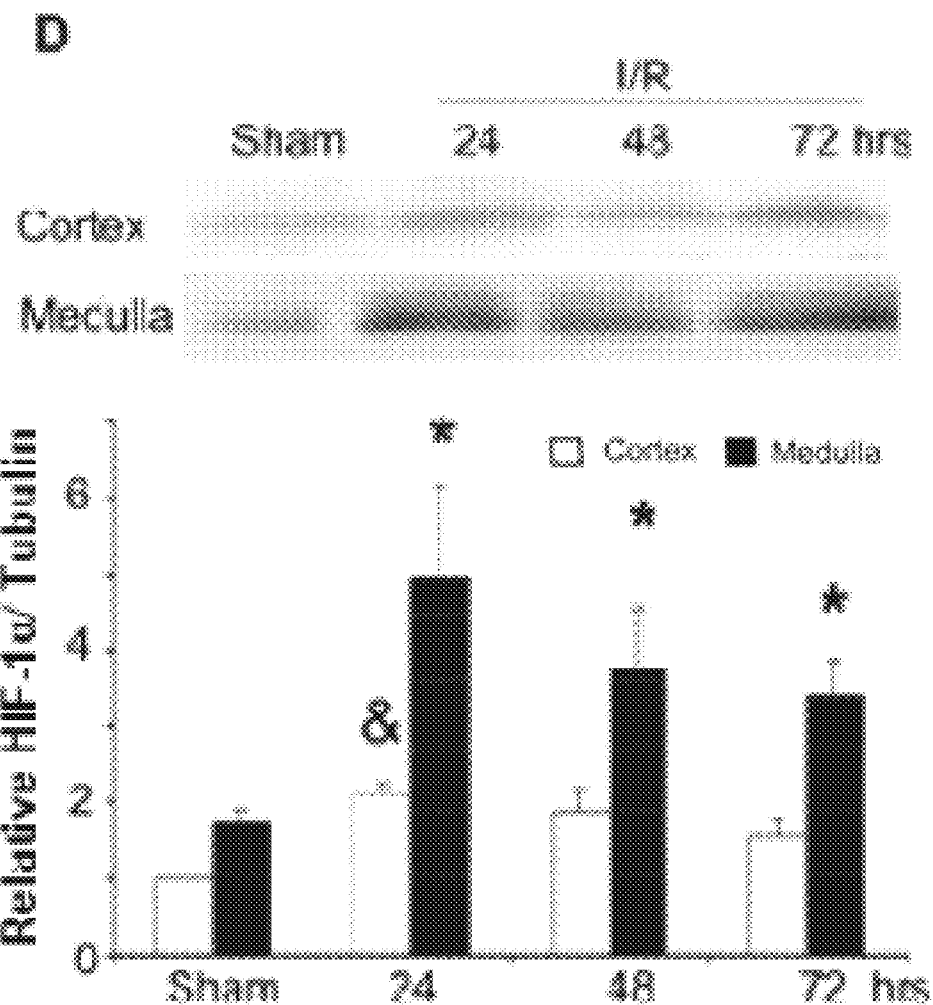
Figure 7:
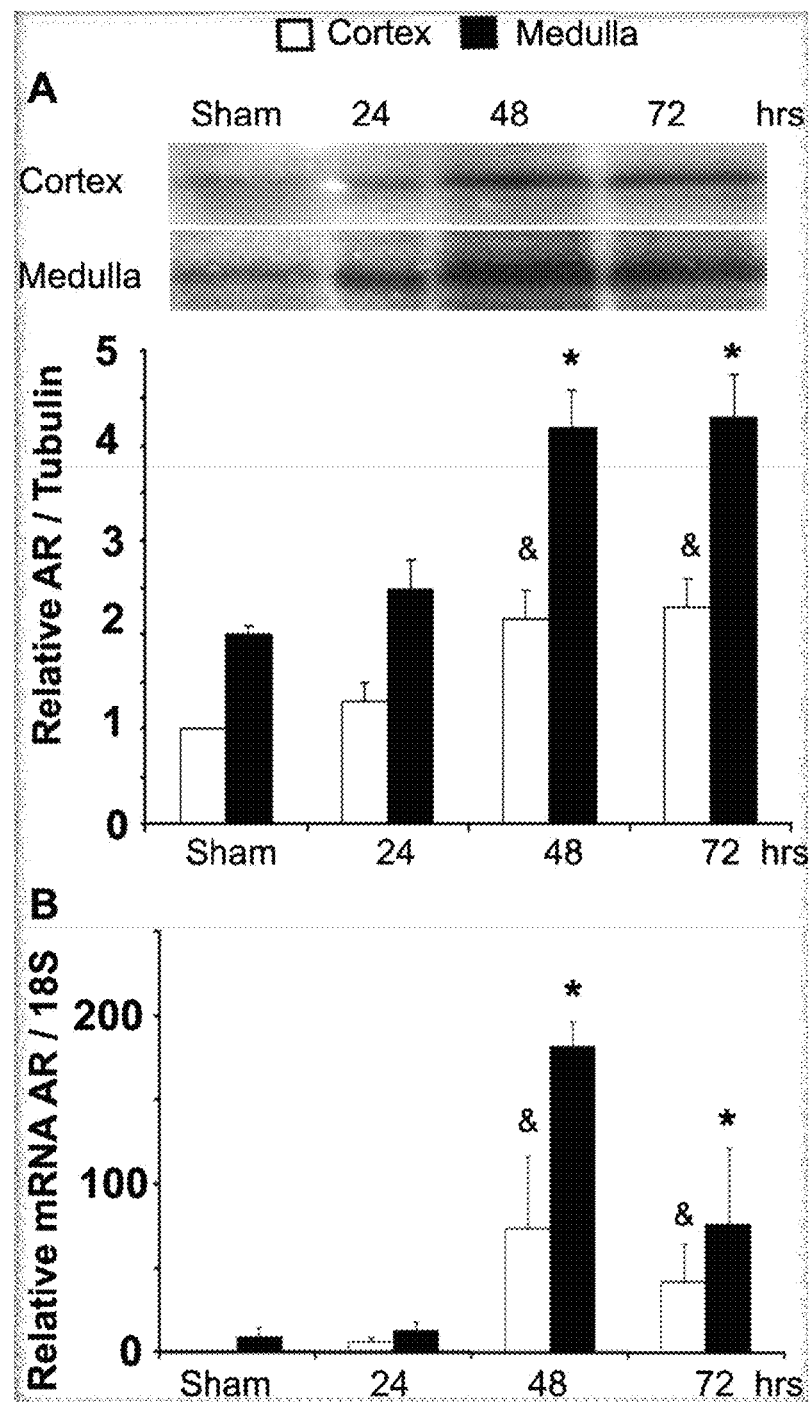
FIG. 7: Experimental I/R induced renal Aldose Reductase (AR) expression. A. AR protein abundance in protein homogenates from cortex and medulla of rat kidney determined by Western blot. A representative picture is shown in the upper section. B. AR mRNA abundance in kidney cortex and medulla measured by qRT-PCR. Mean±SEM. * or & indicates P<0.05; n=5 (*vs sham medulla & vs sham cortex).

Using qRT-PCR and Western blot, we studied the time course activation of NFAT5 in the kidneys of sham and I/R animals. At 24 hrs, kidneys of experimental I/R animals did not have differences in NFAT5 mRNA and protein abundance, as compared with sham animals. However, after 48 hours of reperfusion the abundance of NFAT5 protein (FIG. 6B) and mRNA (FIG. 6C) was significantly increased in cortex and medulla. We also evaluated HIF-1α protein abundance in kidneys with experimental I/R and the results showed significant induction of HIF-1α, both in cortex and medulla (FIG. 6C), peaking after 24 hrs of reperfusion. To evaluate NFAT5 activity in kidneys of experimental I/R animals, we analysed the NFAT5-target gene, Aldose Reductase (AR). In basal conditions AR mRNA and protein abundance was higher in the medulla than the cortex of sham animals (FIG. 7). I/R increased AR expression, both in the cortex and medulla of kidneys in with similar NFAT5 induction timing (FIG. 7).

Finally, we studied ATM and PI3-K (p110α) protein abundance in vivo (experimental I/R) and its activities in vitro (2.5% oxygen in culture cells). Kidneys from I/R animals showed increased ATM and p110α protein abundance in the cortex and medulla (FIG. 8). After 1/R, both proteins increased according to a time course similar to that of NFAT5 induction (FIG. 8B-C). However, p110α was weakly detectable in renal cortex (FIG. 8).

Upregulation of NFAT5 by Low $PO_2$.

Our results showed that anoxia or hypoxia (1 to 2.5% oxygen) induced NFAT5 protein abundance in cultured primary kidney epithelial and HEK293 cells. NFAT5 induction under anoxia/hypoxia was observed when epithelial cells were cultured in isotonic medium and also when cells were cultured in hypertonic media (500 or 640 mOsM). Also, we observed that hypertonicity and hypoxia had additive effects in the induction of NFAT5. All these data suggest that low PO) is a positive regulator of NFAT5 expression, independent of hypertonicity in kidney cells.

The increased NFAT5 abundance caused by anoxia in cultured IMCD cells was associated with its nuclear translocation. Similarly, we found nuclear translocation and reporter assay (OREX luciferase) induced by hypoxia in HEK293 cells, demonstrating strong NFAT5 activation by hypoxia. All these results indicate that low $PO_2$ not only increases the amount of NFAT5 protein, but also triggers its transcriptional activity.

Our studies in HEK293 cells showed that although knocking down the expression of NFAT5 did not affect cell death in isotonic-normoxic conditions, the reduction in NFAT5 expression caused an important increase of apoptosis and necrosis after 8 hrs of hypoxia. These data indicate that NFAT5 has a previously unidentified protective role against hypoxia. Medullary hypoxia is a price that the mammalian kidney pays for efficient urinary concentration (Brezis M, 1993; Brezis M, 1995), and a novel function of NFAT5 in renal medulla would be to improve tolerance to hypertonicity in a hypoxic context.

Upregulation of NFAT5 in Experimental I/R

Figure 5:
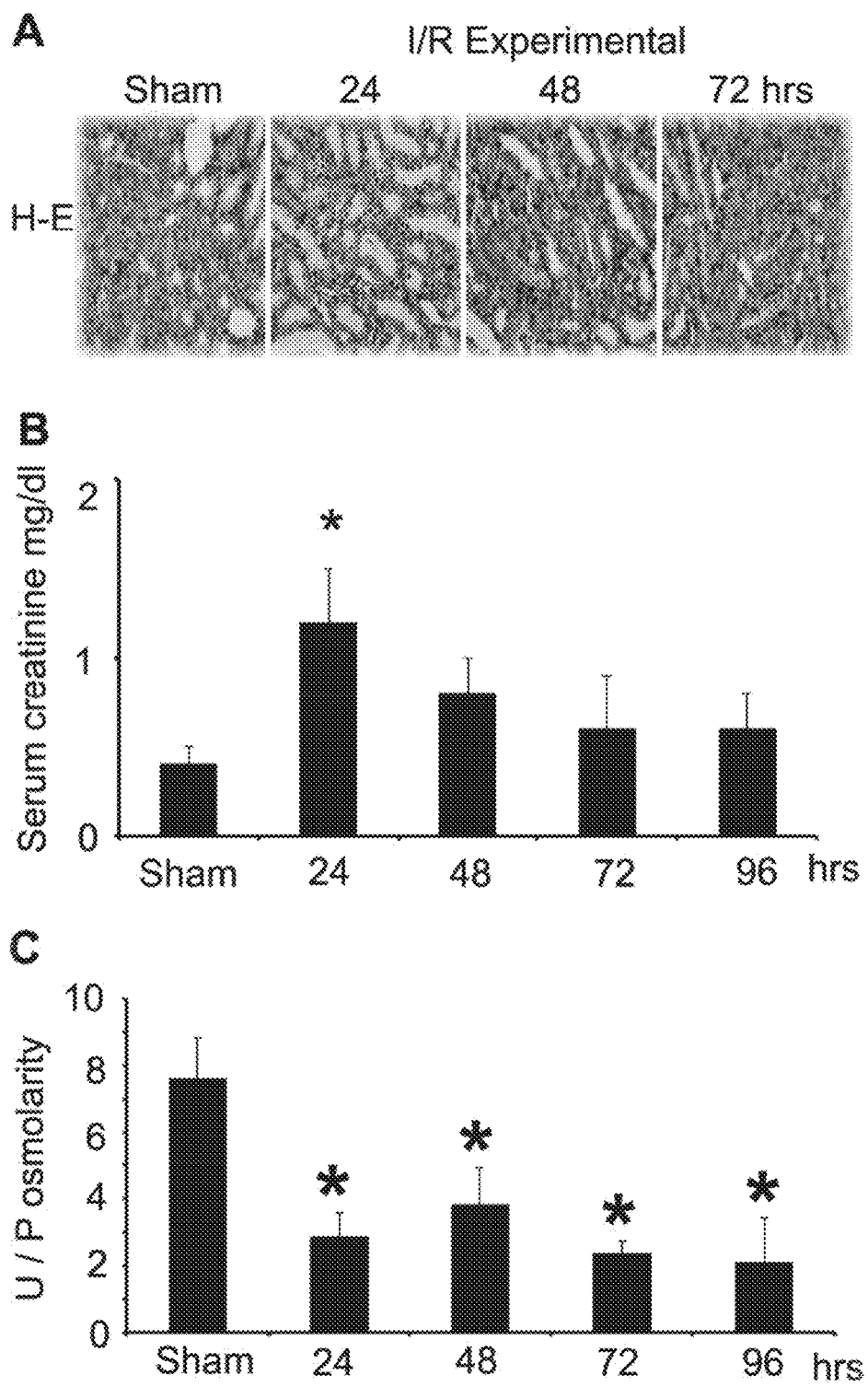
FIG. 5: Kidney function after experimental FR A. Tissue damage evaluated by PAS staining. Brush border, epithelial flattening and mitosis were present in kidneys from I/R animals. B. Serum creatinine (mg/dl) of sham and 24-96 hrs postischemia. C. Urine and plasma ratio (U/P) of osmolality of sham and 24-96 hrs postischemia. Mean±SEM. *, P<0.05; n=5.

To test if hypoxia is a positive regulator of NFAT5 in vivo, we used experimental 1/R induced by temporary bilateral renal ischemia for 30 min. Experimental I/R animals have significantly increased plasma creatinine levels and reduced U/P osmolality, indicating acute renal failure (ARF) (FIG. 5). Our results showed a strong upregulation of NFAT5 protein expression in both cortex and medulla of post-ischemic kidneys (FIG. 6). The induction of NFAT5 was later as compared with HIF1α induction, but persisted up to 72 hours post ischemia. The impairment of urinary concentration ability (reduced U/P osmolality) in experimental I/R animals has been associated with a decreased levels of aquaporins (both in the proximal tubule and collecting duct of post-ischemic kidneys) (Kwon TH, 1999) and sodium transporters [Na,K-ATPase, rat type 1 bumetanide-sensitive Na—K-2Cl cotransporter (BSC-1), Na/H exchanger type 3 (NHE3), and thiazide-sensitive sodium chloride cotransporter (TSC)] (Gong I I, et al., 2004). Our in vivo data indicate that transient hypoxia upregulates NFAT5 expression in isotonic conditions (cortex) and also in the medulla of I/R kidney.

The induction of NFAT5 under hypoxic conditions in vitro and in vivo observed in the present study supports the conclusion that low $PO_2$ is an independent upregulator of NFAT5 in kidney cells and that it could have a protective role.

Consistent with our studies in cultured cells, immunoreactivity of NFAT5 was found in the nucleus of tubules of post-ischemic kidneys, suggesting that NFAT5 protein upregulation is associated with increased transcriptional activity. Further, the NFAT5 upregulation in post-ischemic kidneys was associated with increased expression of AR mRNA and protein (FIG. 6), indicating increased NFAT5 activity.

Mechanism of NFAT5 Activation by Hypoxia.

In the present study, in HEK293 cells the exposure to hypoxia caused a rapid increase of HIF-16 and NFAT5 (mRNA and protein). There is interesting information in the literature suggesting a potential interaction between these two transcription factors: The hypertonic induction of both AQP5 and VEGF in AT2 cells is transcriptionally regulated and mediated, at least in part, by HIF-1α, suggesting a novel role for HIF-1α in modulating cellular adaptive responses to osmotic stress (Zhou B et al, 2007). However, in HEK293 cells we did not found activation of HIF-1α by high-NaCl. We also found that NFAT5 can response to more extreme hypoxia conditions than HIF1, because in HEK293 cells (4 hours of hypoxia), NFAT5 induction is maximal at 1% $O_2$, nevertheless the induction of HIF1 is maximal at 2.5% $O_2$, despite it is induced at 1% $O_2$. On the other hand NFAT5 is induced by hypertonicity and hypoxia, but HIF1 is induced only by hypoxia, therefore, NFAT5 has a more general response to different noxae. Furthermore, NFAT5 is basically expressed in all tissues, and HIF1 is not. This situation allows NFAT5 to react faster than HIF1 to the noxa. This preliminary information suggests that NFAT5 and HIF-1α activation by hypoxia might be inducing by different pathways. We are currently studying this hypothesis.

Figure 3:
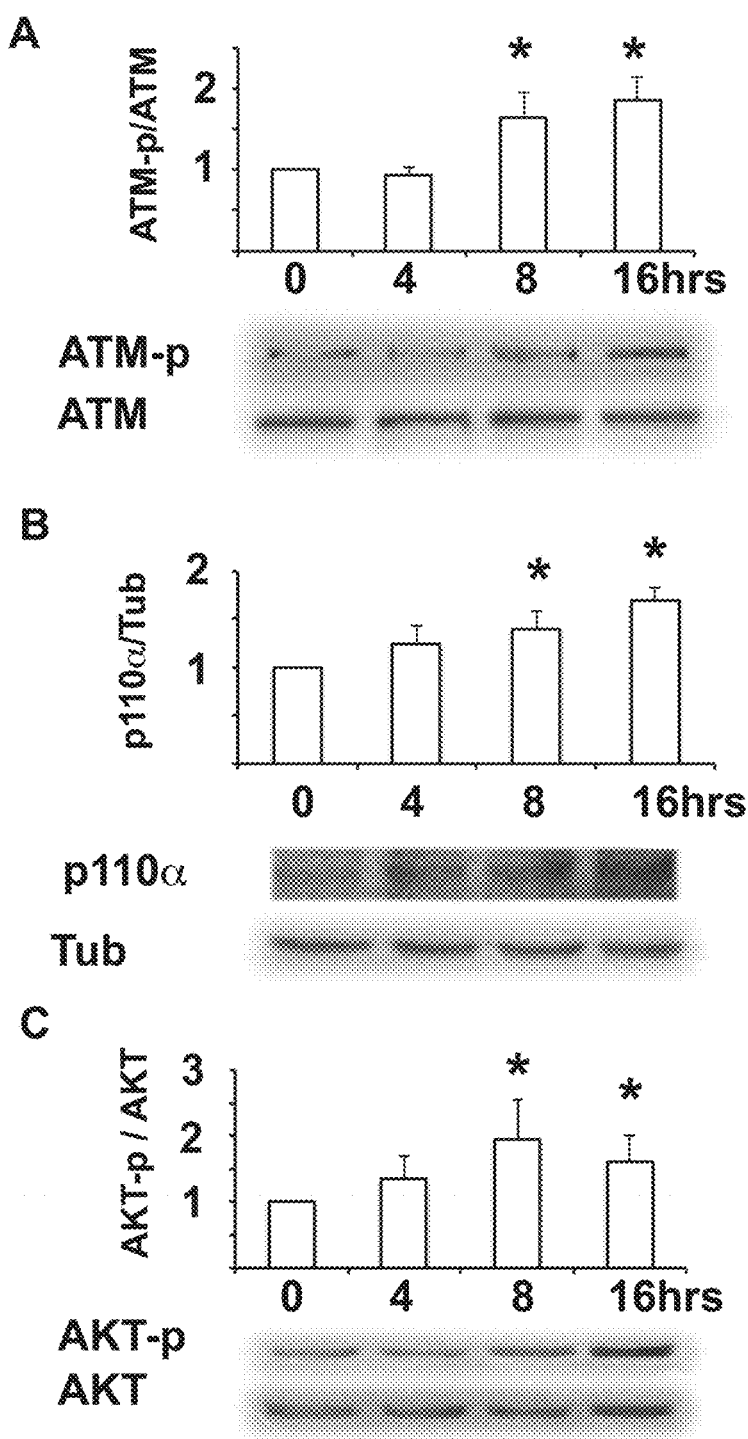
FIG. 3: NFAT5-regulators protein, ATM and PI3-K, are induced in HEK293 cells by hypoxia. HEK293 cells cultured at 300 mosmol were exposed for 0, 4, 8 and 16 hrs to hypoxia (2.5% of PO2). A. Time course response of ATM phosphorylation (normalized by total ATM) was measured by Western blot. B. Time course response of PI3-K activation was measured by Western blot of p110α protein abundance (normalized by tubulin: Tub). C. AKT-308 phosphorylation (normalized by total AKT) was measured by Western blot. A representative picture is shown in the upper section. Mean±SEM. *, P<0.05; n=5.

Our results in post-ischemic kidneys demonstrated that both ATM and PI3K (p110α) were induced in I/R kidneys (FIG. 8). We also found ATM and PI3-K activation in HEK293 cells exposed to hypoxia (2.5% oxygen) (FIG. 3). ATM activation has also previously been described during exposure to hypoxia (Hammond, E M, 2003; Bindra R S, 2007; Hammond E M, 2004). Recent studies in cancer cells demonstrate alternate mechanisms for activating ATM under hypoxic conditions, including the increase of radical oxygen species, oxidative stress and DNA breaks (Bhoumik A, 2007). In cancer cells exposed to hypoxia, ATM remains diffuse throughout the nucleus, as does phosphorylated ATM (Bencokova Z, 2009). This localization pattern is reminiscent of that seen in response to high salt (Bencokova Z, 2009), indicating that hypoxia and osmotic stress may share a similar mechanism of ATM activation. So, our results and others demonstrate ATM and PI3-K activation by hypoxia, suggesting its participation in NFAT5 activation by this stimulus.

NFAT5 belongs to the nuclear factor of activated T-cells (NFAT). NFAT proteins were originally defined as calcium/calcineurin-dependent regulators of cytokine gene transcription in T lymphocytes. NFAT5 can be induced in both primary quiescent T lymphocytes and differentiated Th1 and Th2 cell populations upon mitogen- or antigen receptor-dependent activation (Trama J, 2002). However, induction of NFAT5 by a hyperosmotic stimulus in cultured epithelial cells is not blocked by the inhibition of calcineurin (Trama J, 2002). Further studies are needed to clarify if hypoxia activates calcineurin-dependent mechanisms for NFAT5 induction/activation in kidney cells.

These results demonstrate for the first time that NFAT5 is induced by hypoxia and it has a potential protective role against ischemic damage.

Example 2

NAFT5 is Induced in Heart, Brain, Skin, and Lymphocytes Hypoxia

Animals.

Adult male Sprague-Dawley rats (250 g, n=5 for each) were housed in a 12 hrs light/dark cycle. The animals had food ad libitum and controlled water and were maintained at the University animal care facility. All experimental procedures were in accordance with institutional and international standards for the humane care and use of laboratory animals (Animal Welfare Assurance Publication A5427-01, Office for Protection from Research Risks, Division of Animal Welfare, The National Institutes of Health).

Myocardial Infarction.

The myocardial infarction was induced (MI group), as described previously (Bhindi R, 2006). Rats were anesthetized by i.p. injection of ketamine and xylazine (50 and 10 mg/kg, respectively) and ventilated with room air using a small animal mechanical ventilator (Columbus Instruments Model 121). Left thoracotomy was performed at the fourth intercostal space, the pericardium was opened and the left anterior descending coronary artery was tied with 6.0 silk suture (Hospital & Diagnostics Supplies Ltd). Following coronary occlusion, the chest was sutured by planes and after awakening and extubation, animals received tramadol (5 mg/kg weight) orally for analgesia. Sham (Sh) operated rats underwent the same procedure, but were produced without artery ligation.

Animal Euthanasia and Samples Collection

For euthanasia, animals were anesthetized with ketamine and xylazine (50 mg/kg and 10 mg/kg) i.p. The hearts were stopped by intraventricular injection of potassium chloride solution (10%), according to the American Veterinary Medical Association (AVMA) Guidelines on Euthanasia. The hearts with transmural infarction of left ventricular (LV) were included in the study in order to evaluate only infarctions (Schoemaker R G, 1990). The LV was then dissected and used for RNA extraction. Analogous region was used from Sh group samples.

Quantitative Real Time PCR (qRT-PCR)

Total RNA was isolated using TRIzol (GIBCO, Life Sciences) as per manufacturer instructions. RNA concentration was determined by spectrophotometry and integrity of the RNA was assessed by agarose gel electrophoresis. cDNA was prepared from total RNA (0.5 μg) using a reverse transcription system (random hexamers, Improm II Reverse Transcriptase System; Promega). PCR was performed on 8 ng and 80 ng cDNA samples per 20:1 reaction in triplicate for each experiment (GoTaq Flexi DNA polymerase, Promega). Amplicons were detected for Real-Time Fluorescence Detection (Rotor-Gene Q, Qiagen). Primers used to qPCR were:

```
to NFAT5:
SEQ ID NO: 3:   5'-TTCATCTCATTGCTCAGCG-3'
and
SEQ ID NO: 4:   5'-GGGAGAAGATCATAGACAGATTC-3'
and to 18S (housekeeping):
SEQ ID NO: 7:   5'-TTAGAGTGTTCAAAGCAGGCCCGA-3'
and
SEQ ID NO: 8:   5'-TCTTGGCAAATGCTTTCGCTCTGG-3'.
```

The detection system records the number of PCR cycles (Ct) required to produce an amount of product equal to a threshold value, which is a constant. From the Ct values, we calculated the relative mRNA abundance in each experimental condition, and values were normalized to the relative abundance of each transcript in tissue from paired sham animals, as described (Irarrazahal C, 2010).

Neuronal Cultures

Primary cultures of cortical neurons were obtained from day-18 embryos of Sprague-Dawley rats as described (Banker and Goslin 1988).

Lymphocytes Cultures

Lymphoid cells of peripheral blood were purified by Ficoll-Hypaque density gradient centrifugation as described by manufactured (Amersham, Biosciences). Purified lymphocytes were cultured in alpha-MEM in 10% SFB by 24 hours. After this time the lymphocytes cultured were exposed to hypoxia conditions.

Primary Human Fibroblast from Skin.

The fibroblasts were obtained from skin from healthy donors. Cell cultures were performed in DMEM-red phenol supplemented by 10% of Serum fetal bovine, penicillin-streptomycin 0.1 mg/ml, fungizone 0.25 μl/ml and glutamaz 2 mM. The cell cultures were exposed to hypoxia condition.

Hypoxia in Cell Cultures

Cultured cells were incubated in isotonic (300 mOsM) and normoxic condition (21% $O_2$). After 24 his of culture in isotonic media, cells were incubated in hypoxic (1% $O_2$) conditions for 8 hours at 37° C. Hypoxic conditions were obtained by replacing oxygen with $N_2$, using a Heracell 150i $CO_2$ incubator (Thermo Scientific).

Western Blot Analysis

Total protein was measured using the BCA Protein Assay Kit, (Pierce, Rockford, Ill.). Cell culture were homogenized with an Ultra-Turrax homogenizer in lysis buffer containing 50 mM Tris-HCl, pH 8.0, 150 mM NaCl, 1% Triton X-100, protease inhibitor (Complete Mini, Roche Applied Science, Indianapolis, Ind.), and phosphatase inhibitor cocktails (Phosphatase Inhibitor Cocktails 1 & 2, Sigma, St. Louis, Mo.). Cell homogenates were then centrifuged (15,000×g, 10 min) and the supernatant was stored (−70° C.) for SDS_PAGE and Western blot analysis. Proteins were separated on 7.5 or 10% Tris-Glycine gels and transferred to nitrocellulose membranes (Invitrogen, Carlsbad, Calif.). Western blot analysis was performed according to standard conditions (Irarrazabal C, 2010). In brief, after blocking nonspecific binding, membranes were incubated with rabbit anti-NFAT5 (NFAT5) (Affinity BioReagents, Golden, Colo.) or rabbit anti-tubulin (Cell Signalling), overnight at 4° C. After washing with 0.1% Tween-20 in PBS, blots were incubated with the appropriate horseradish peroxidase (HRP)-conjugated secondary antibody for 1 hour at room temperature. Proteins were detected using an enhanced chemiluminescence technique (PerkinElmer, Life Sciences, Boston, Mass.). The blots were scanned and densitometric analysis was performed using the public domain NIH Image program v1.61 (US National Institutes of Health, rsb.info-.nih.gov/nih-image).

Statistical Analysis

Data are expressed as average±SEM. Values from different groups were assessed with the parametric Student's t-test when comparing two groups and Anova for multiple comparisons with a post-hoc Fisher's test when comparing more than two groups. The significance level was $p < 0.05$.

Effect of Hypoxia on NFAT5.

NFAT5 Expression is Induced in Myocardial Infarction (MI).

Figure 9:
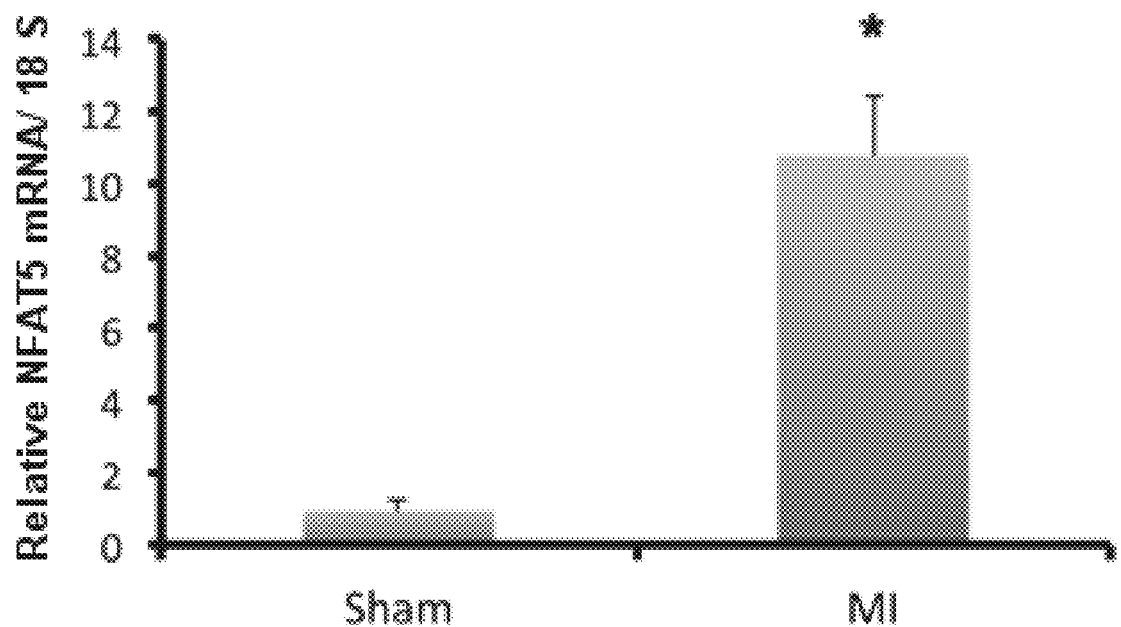
FIG. 9: Myocardial infarction induced NFAT5. The mRNA levels of NFAT5 were measured by qRT-PCR in left ventricular from Sham and myocardial infarction (MI) animals (n=5, p>0.05).

We measured the mRNA expression of NFAT5 in tissue samples from left ventricular of sham and infarcted rats after one week of MI by qRT-PCR. The FIG. 9, showed that MI significantly increased the NFAT5 mRNA levels in MI compared with Sham tissue (10.96±1.6 vs 0.9±0.33, $p < 0.05$), suggesting that infarcted tissue induced the NFAT5 gene expression.

NFAT5 Expression is Induced by Hypoxia in Primary Cultures of Cortical Neurons.

Figure 10:
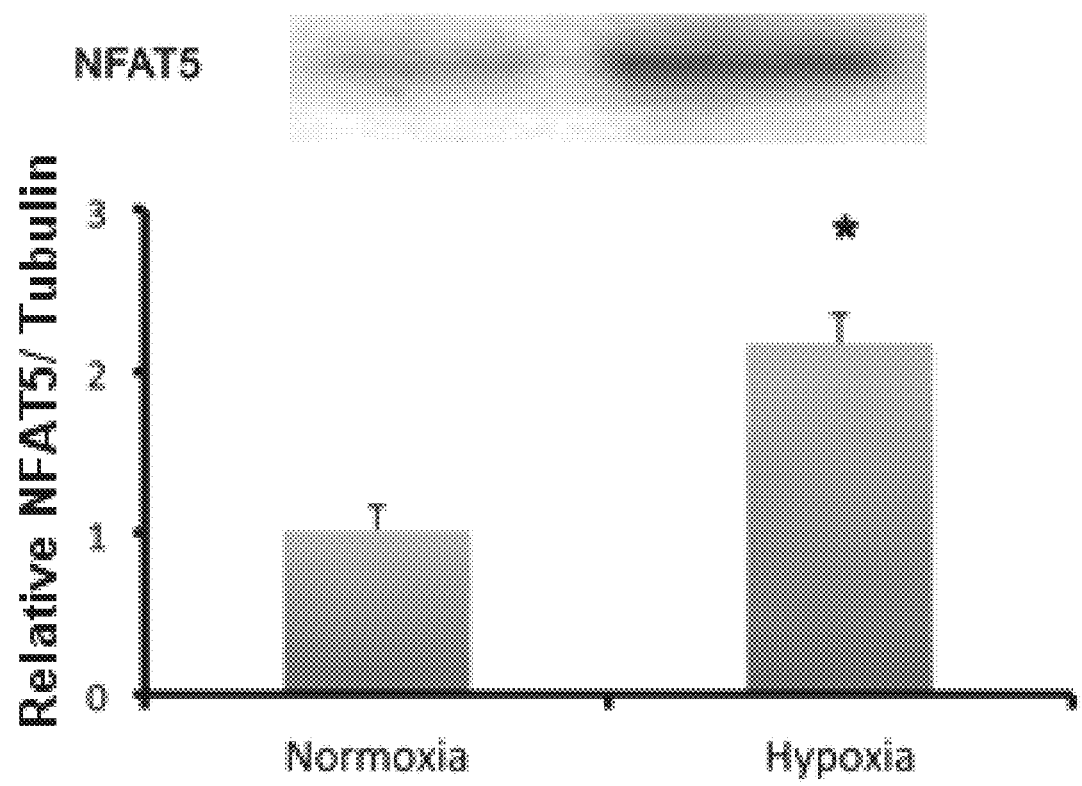
FIG. 10: Hypoxia induced NFAT5 in primary cultures of cortical neurons. The protein levels of NFAT5 were measured by Western blot in primary cultured cortical neurons from rat, exposed to normoxia (21% $O_2$) and hypoxia (1% $O_2$) by 8 hrs (n=3, p>0.05).

We analysed the effect of hypoxia (1% of $O_2$) on the NFAT5 protein abundance in primary cultures of cortical neurons from rat brain by Western blot. Cortical neurons were cultured in normoxic (21% of $O_2$) or hypoxic (1% of $O_2$) conditions by 8 hrs. The hypoxia condition induced the NFAT5 protein abundance (FIG. 10).

NFAT5 Expression is Induced by Hypoxia in Human Lymphocytes

Figure 11:
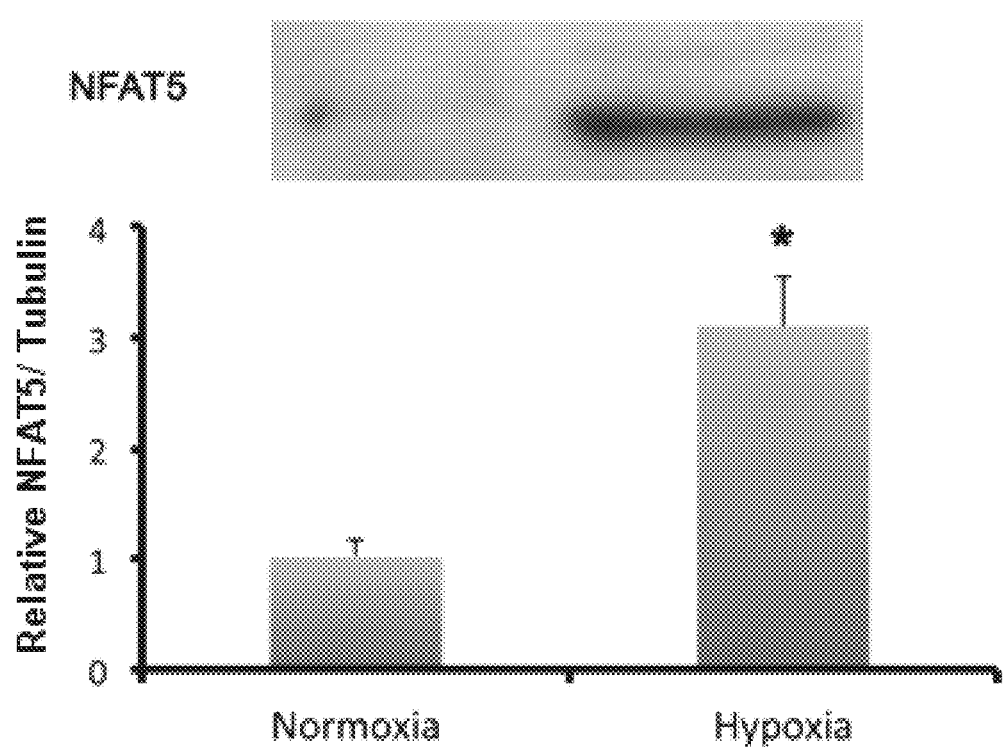
FIG. 11: Hypoxia induced NFAT5 in primary cultures of purified lymphocyte. The protein levels of NFAT5 were measured by Western blot in primary cultured lymphocytes from human, exposed to normoxia (21% $O_2$) and hypoxia (1% $O_2$) by 8 hrs (n=3, p>0.05).

We analysed the effect of hypoxia (1% of $O_2$) on the NFAT5 protein abundance in primary cultures of human lymphocytes by Western blot. Human lymphocytes were cultured in normoxic (21% of $O_2$) or hypoxic (1% of $O_2$) conditions by 8 hrs. Hypoxia condition induced the NFAT5 protein abundance (FIG. 11).

NFAT5 Expression is Induced by Hypoxia in Primary Cultures of Fibroblast of Human Skin.

Figure 12:
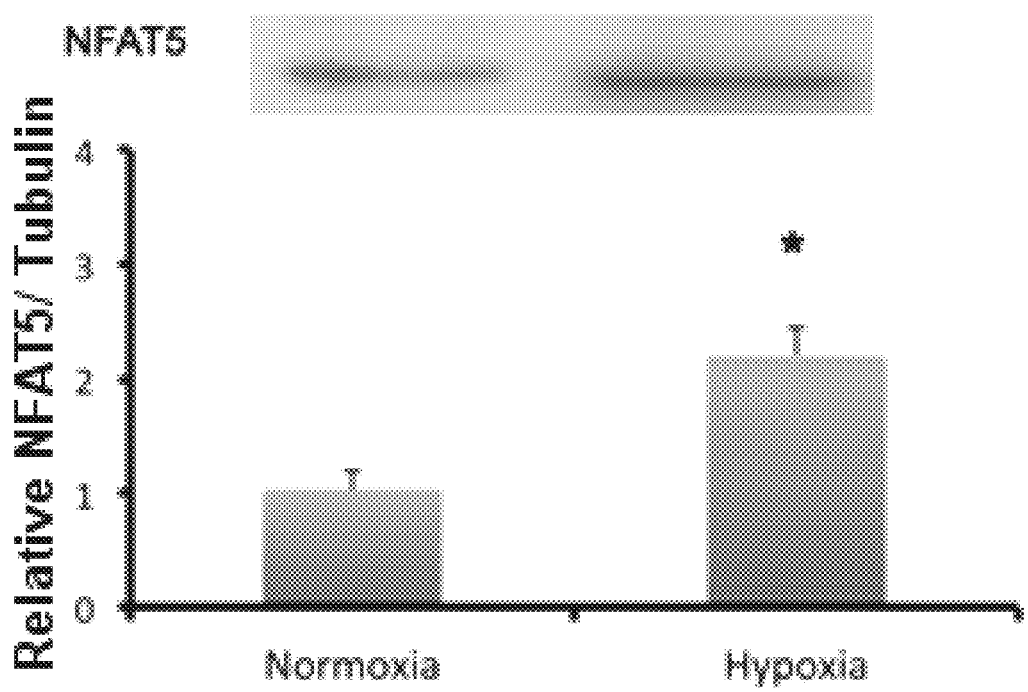
FIG. 12: Hypoxia induced NFAT5 in primary cultures of fibroblast. The protein levels of NFAT5 were measured by Western blot in primary cultured skin fibroblast from human, exposed to normoxia (21% $O_2$) and hypoxia (1% $O_2$) by 8 hrs (n=3, p>0.05).

We studied the effect of hypoxia (1% of $O_2$) on the NFAT5 protein abundance in primary cultures of cultures of fibroblast of human skin by Western blot. Human fibroblasts were cultured in normoxic (21% of $O_2$) or hypoxic (1% of $O_2$) conditions by 8 hrs. hypoxia condition induced the NFAT5 protein abundance (FIG. 12).

DISCUSSION

The present information shown that NFAT5 was induced in left ventricular exposed to myocardial infarction in rat suggesting that NFAT5 is involved in the acute response to ischemic condition in hearth and it could be used as a biomarker of this severe heart condition. Additionally, NFAT5 was also induced in a primary culture of cortical neurons from rat brain suggesting that this kind of neurons response to hypoxia damage inducing the expression of this factor and it could be used as biomarker of hypoxia condition of brain. Finally, we tested the effect of hypoxia on other two human cells (lymphocytes and fibroblast) and demonstrated that hypoxia can induce the expression of this factor suggesting that many cell types induces the NFAT5 gene expression to low oxygen tension condition. These results can let propose that NFAT5 as biomarker of hypoxia of many tissue.

REFERENCES

Araujo M and Welch Wj. Oxidative strees and nitric oxide in kidney function. Curr Opin Nephrol Hypertens 15:72-77, 2006.

Banker G. and Goslin K. Developments in neuronal cell culture. Nature 336, 185-186. CrossRef, PubMed, CAS, Web of Science® Times Cited: 67, ADS, 1988.

Bencokova Z, Kaufmann M R, Pires I M, Lecane P S, Giaccia A J, Hammond E M. ATM activation and signalling under hypoxic conditions. Mol Cell Biol. 29: 526-37, 2009.

Bhindi R, Witting P K, McMahon A C, Khachigian L M, Lowe H C. Rat models of myocardial infarction. Thromb Haemost 96: 602-610, 2006.

Bhoumik A, Lopez-Bergami P, Ronai Z. ATF2 on the double-activating transcription factor and DNA damage response protein. Pigment Cell Res. 20: 498-506, 2007.

Bindra R S, Crosby M E, Glazer P M. Regulation of DNA repair in hypoxic cancer cells. Cancer Metastasis Rev. 26:249-60, 2007.

Brezis M, Epstein F H. Cellular mechanisms of acute ischaemic injury in the kidney. Annu Rev Med; 44: 27-37, 1993.

Brezis M, Rosen S. Hypoxia of the renal medulla-its implications for disease. N End J Med. 332: 647-55, 1995.

Burg M B, Ferraris J D, Dmitrieva N I. Cellular response to hyperosmotic stresses. Physiol Rev. 87: 1441-74, 2007.

Cai Q, Ferraris J D, Burg M B. High NaCl increases NFAT5 mRNA and protein by stabilizing its mRNA. Am J Physiol Renal Physiol. 2005 October; 289(4):F803-7, 2005.

Cha Et Woo S K, Han K H, Kim Y H, Handler J S, Kim J, Kwon H M. Hydration status affects nuclear distribution of transcription factor tonicity responsive enhancer binding protein in rat kidney. J Am Soc Nephrol. 12: 2221-30, 2001.

Chen Y, Schnetz M P, Irarrazabal C E, Shen R F, Williams C K, Burg M B, Ferraris J D. Proteomic identification of proteins associated with the osmoregulatory transcription factor NFAT5: functional effects of Hsp90 and PARP-1. Am J Physiol Renal Physiol. 292: F98192.2007.

Colla E, Lee S D, Sheen M R, Woo S K, Kwon H M. NFAT5 is inhibited by RNA helicase A via interaction involving the ET loop. Biochem J. 393: 411-9, 2006.

Dahl S C, Handler J S, Kwon H M. Hypertonicity-induced phosphorylation and nuclear localization of the transcription factor NFAT5. Am J Physiol Cell Physiol. 280: C248-53, 2001.

Ferraris J D, Williams C K, Martin B M, Burg M B, García-Pérez A. Cloning, genomic organization, and osmotic response of the aldose reductase gene. Proc Natl Acad Sci USA. 91:10742-6, 1994.

Ferraris J D, Williams C K, Jung K Y, Bedford J J, Burg M B, García-Pérez A.ORE, a eukaryotic minimal essential osmotic response element. The aldose reductase gene in hyperosmotic stress. J Biol. Chem. 271:18318-21, 1996.

Ferraris J D, Williams C K, Ohtaka A, García-Pérez A. Functional consensus for mammalian osmotic response elements. Am J. Physiol. 276:C667-73, 1999.

Ferraris J D, Williams C K, Persaud P, Zhang Z, Chen Y, Burg M B. Activity of the NFAT5 transactivation domain varies directly with extracellular NaCl concentration. Proc Natl Acad Sci USA. 99: 739-44, 2002a.

Ferraris J D, Persaud P, Williams C K, Chen Y, Burg M B. cAMP-independent role of PKA in tonicity-induced transactivation of tonicity-responsive enhancer/osmotic response element binding protein. Proc Natl Acad Sci USA. 99:16800-5, 2002b.

Gong H, Wang W, Kwon T H, Jonassen T, Li C, Ring T, FrøkiAEr J, Nielsen S. EPO and alpha-MSH prevent ischemia/reperfusion-induced down-regulation of AQPs and sodium transporters in rat kidney. Kidney Int. 66:683-95, 2004.

Hammond E M, Doric M J, & Giaccia A J. ATR/ATM targets are phosphorylated by ATR in response to hypoxia and ATM in response to reoxygenation. Journal of Biological Chemistry. 278: 12207-12213, 2003.

Hammond E M and Giaccia A J. The role of ATM and ATR in the cellular response to hypoxia and re-oxygenation. DNA Repair (Amst). 3: 1117-22, 2004.

Irarrazabal C E, Liu J C, Burg M B, Ferraris J D. ATM, a DNA damage-inducible kinase, contributes to activation by high NaCl of the transcription factor NFAT5/OREBP. Proc Natl Acad Sci USA. 101: 8809-14, 2004.

Irarrazabal C E, Burg M B, Ward S G, Ferraris J D. Phosphatidylinositol 3-kinase mediates activation of ATM by high NaCl and by ionizing radiation: Role in osmoprotective transcriptional regulation. Proc Natl Acad Sci USA. 103: 8882-7, 2006.

Irarrazabal C E, Williams C K, Ely M A, Birrer M J, García-Pérez A, Burg M B, Ferraris J D. Activator protein-1 contributes to high NaCl-induced increase in tonicity-responsive enhancer/osmotic response element-binding protein transactivating activity. J Biol. Chem. 283: 2554-63, 2008.

Irarrazabal C E, Gallazzini M, Schnetz M P, Kunin M, Simons B L, Williams C K, Burg M B, Ferraris J D. Phospholipase C-gammal is involved in signaling the activation by high NaCl of the osmoprotective transcription factor NFAT5. Proc Natl Acad Sci USA. 107:906-11, 2010.

Ko B C, Turck C W, Lee K W, Yang Y, Chung S S. Purification, identification, and characterization of an osmotic response element binding protein. BiochemBiophys Res Cornmun. 270:52-61, 2000.

Ko B C, Lam A K, Kapus A, Fan L, Chung S K, Chung S S. Fyn and p38 signaling are both required for maximal hypertonic activation of the osmotic response element-binding protein/tonicity-responsive enhancer-binding protein (OREBP/NFAT5). J Biol. Chem. 277: 46085-92, 2002.

Kwon T H, Frøkiaer J, Fernandez-Llama P, Knepper M A, Nielsen S. Reduced abundance of aquaporins in rats with bilateral ischemia-induced acute renal failure: prevention by alpha-MSH. Am J. Physiol. 277: F413-27, 1999.

Lam A K, Ko B C, Tam S, Morris R, Yang J Y, Chung S K, Chung S S. Osmotic response element-binding protein (OREBP) is an essential regulator of the urine concentrating mechanism. J Biol Chem. 279: 48048-54, 2004.

Lopez-Rodriguez C. Antos C L, Shelton J M, Richardson J A, Lin F, Novobrantseva T I, Bronson R T, Igarashi P, Rao A, Olson E N. Loss of NFAT5 results in renal atrophy and lack of tonicity-responsive gene expression. Proc Natl Acad Sci USA. 101: 2392-7, 2004.

Miyakawa H, Woo S K, Dahl S C, Handler J S, Kwon H M. Tonicity-responsive enhancer binding protein, a rel-like protein that stimulates transcription in response to hypertonicity. Proc Natl Acad Sci USA. 96: 2538-42, 1999.

Pettigrew L C, Kindy M S, Scheff S, Springer J E, Kryscio R J, et al. Focal cerebral ischemia in the TNFalpha-transgenic rat. J Neuroinflammation 5:47, 2008.

Priyadarshi A, Periyasamy S, Burke T J, Britton S L, Malhotra D, Shapiro J I. Effects of reduction of renal mass on renal oxygen tension and erythropoietin production in the rat. Kidney Int. 61:542-6, 2002.

Rosas-Rodríguez J A, Valenzuela-Soto E M. Enzymes involved in osmolyte synthesis: how does oxidative stress affect osmoregulation in renal cells? Life Sci. 87: 515-20, 2010.

Sadowski J. Estimation of changes in renal tissue electrolytes from measurements of electrical admittance: application in the rat. Acta Physiol Pol. 36: 339-44, 1985.

Schoemaker R G, Urquhart J, Debets J J M, Struyker Boudier H A J, Smits J F M. Acute hemodynamic effects of coronary artery ligation in conscious rats. Basic Res Cardiol 85: 9-20, 1990.

Sykes E, Cosgrove J F. Acute renal failure and the critically ill surgical patient. Ann R CollSurgEngl; 89: 22-29, 2007.

Thygesen K, Alpert J S, White H D on behalf of the Joint ESC/ACCF/AHA/WHF Task Force for the Redifinition of Myocardial Infarction. Universal definition of myocardial infarction. Eur Heart J 28: 2525-2538, 2007.

Tian D-S, Dong Q, Pan D-J, He Y, Yu Z-Y, et al. Attenuation of astrogliosis by suppressing of microglial proliferation with the cell cycle inhibitor olomoucine in rat spinal cord injury model. Brain Res. 1154:206-214, 2007.

Trama J, Go W Y, Ho S N. The osmoprotective function of the NFAT5 transcription factor in T cell development and activation. J. Immunol. 169:5477-88, 2002.

Villanueva 5, Céspedes C, Vio C P. Ischemic acute renal failure induces the expression of a wide range of nephrogenic proteins. Am J Physiol Regul Integr Comp Physiol. 290:R861-70, 2006.

Woo S K, Dahl S C, Handler J S, Kwon H M. Bidirectional regulation of tonicity-responsive enhancer binding protein in response to changes in tonicity. 1: Am J Physiol Renal Physiol. 278:F1006-12, 2000a.

Woo S K, Nahm O, Kwon H M. How salt regulates genes: function of a Rel-like transcription factor NFAT5. Biochem Biophys Res Commun. 278: 269-71, 2000b.

Yang Y, Jalal F Y, Thompson J F, Walker E J, Candelario-Jalil E, et al. Tissue inhibitor of metalloproteinases-3 mediates the death of immature oligodendrocytes via TNF-αJTACE in focal cerebral ischemia in mice. J. Neuroinflammation. 8:108, 2011.

Zhang Z, Ferraris J D, Irarrazahal C E, Dmitrieva N I, Park J H, Burg M B. Ataxia telangiectasia-mutated, a DNA damage-inducible kinase, contributes to high NaCl-induced nuclear localization of transcription factor NFAT5/OREBP. Am J Physiol Renal Physiol. 289: F506-11, 2005.

Zhou X, Ferraris J D, Cai Q, Agarwal A, Burg M B. Increased reactive oxygen species contribute to high NaCl-induced activation of the osmoregulatory transcription factor NFAT5/OREBP. Am J Physiol Renal Physiol. 289: F377-85, 2005.

Zhou X, Ferraris J D, Burg M B. Mitochondrial reactive oxygen species contribute to high NaCl-induced activation of the transcription factor NFAT5. Am J Physiol Renal Physiol. 290: F1169-76, 2006.

Zhou B, Ann D K, Li X, Kim K J, Lin H, Minoo P, Crandall E D, Borok Z. Hypertonic induction of aquaporin-5: novel role of hypoxia-inducible factor-1 alpha. 1: Am J Physiol Cell Physiol. 292: C1280-90, 2007.

---

The invention claimed is:

1. A method for detecting and/or quantifying NFAT5 (Nuclear factor of activated T-cells 5) in a subject previously exposed to hypoxia, the method comprising
   a) providing a body sample from a subject previously exposed to hypoxia;
   b) concentrating the transcription factors or RNA present in the sample to form a treated sample; and
   c) detecting and/or quantifying NFAT5 or NFAT5 RNA in the treated sample.

2. The method according to claim 1, wherein the body sample is selected from the group consisting of: blood, urine, gingival crevicular fluid, saliva, synovial fluid, amniotic fluid, and tissue.

3. The method according to claim 1, wherein the transcription factors present in the sample are concentrated by or using an approach selected from the group consisting of: laboratory methods and devices useful in separating larger elements from the sample, immunopurification methods, immunoprecipitation methods, centrifugation, centrifuge tubes, ultracentrifugation, microfiltration, microfilter cartridges, microfilter columns, and other microfilter media up to 0.22 μm.

4. The method according to claim 1, wherein the detection and/or quantification of NFAT5 in the treated sample is performed by a primary antibody directed to NFAT5, and a secondary antibody conjugated with a label, directed to the primary antibody; the label being selected from the group consisting of: a fluorescent marker, an enzyme, a radioactive marker, a chemical compound, and an infrared compound.

5. The method according to claim 4, wherein the primary antibody is conjugated directly with a label, in which case, the secondary antibody is not needed; the label being selected from the group consisting of: a fluorescent marker, an enzyme, a radioactive marker, a chemical compound, and an infrared compound.

6. The method of claim 1, wherein the tissue is selected from the group consisting of heart, kidney, brain, lymphoid and skin.

7. The method of claim 1, wherein the RNA is mRNA.

8. The method of claim 7, wherein the mRNA is detected by PCR.

9. The method of claim 8, wherein the PCR is qRT-PCR.

\* \* \* \* \*

SEQUENCE LISTING

<160> NUMBER OF SEQ ID NOS: 8

<210> SEQ ID NO 1
<211> LENGTH: 24
<212> TYPE: DNA
<213> ORGANISM: Human

<400> SEQUENCE: 1
attcgtccac cacagcttca gact                                              24

<210> SEQ ID NO 2
<211> LENGTH: 24
<212> TYPE: DNA
<213> ORGANISM: Human

<400> SEQUENCE: 2
agcaatgagg acatggccac tcta                                              24

<210> SEQ ID NO 3
<211> LENGTH: 19
<212> TYPE: DNA

```
<213> ORGANISM: Human

<400> SEQUENCE: 3
ttcatctcat tgctcagcg                                              19

<210> SEQ ID NO 4
<211> LENGTH: 23
<212> TYPE: DNA
<213> ORGANISM: Human

<400> SEQUENCE: 4
gggagaagat catagacaga ttc                                         23

<210> SEQ ID NO 5
<211> LENGTH: 19
<212> TYPE: DNA
<213> ORGANISM: Human

<400> SEQUENCE: 5
acctctggac ttgcctttc                                              19

<210> SEQ ID NO 6
<211> LENGTH: 19
<212> TYPE: DNA
<213> ORGANISM: Human

<400> SEQUENCE: 6
tttttcttgt cgttcgcgc                                              19

<210> SEQ ID NO 7
<211> LENGTH: 24
<212> TYPE: DNA
<213> ORGANISM: Human

<400> SEQUENCE: 7
ttagagtgtt caaagcaggc ccga                                        24

<210> SEQ ID NO 8
<211> LENGTH: 24
<212> TYPE: DNA
<213> ORGANISM: Human

<400> SEQUENCE: 8
tcttggcaaa tgctttcgct ctgg                                        24
```